United States Patent
Guthrie et al.

(10) Patent No.: US 11,725,025 B2
(45) Date of Patent: *Aug. 15, 2023

(54) PROGESTERONE PHOSPHATE ANALOGS AND USES RELATED THERETO

(71) Applicant: EMORY UNIVERSITY, Atlanta, GA (US)

(72) Inventors: David Brian Guthrie, Avondale Estates, GA (US); Mark Andrew Lockwood, Johns Creek, GA (US); Michael G. Natchus, Alpharetta, GA (US); Dennis C. Liotta, Atlanta, GA (US); Donald G. Stein, Atlanta, GA (US); Iqbal Sayeed, Atlanta, GA (US)

(73) Assignee: Emory University, Atlanta, GA (US)

( * ) Notice: Subject to any disclaimer, the term of this patent is extended or adjusted under 35 U.S.C. 154(b) by 114 days.

This patent is subject to a terminal disclaimer.

(21) Appl. No.: 17/360,614

(22) Filed: Jun. 28, 2021

(65) Prior Publication Data

US 2021/0395294 A1    Dec. 23, 2021

Related U.S. Application Data

(63) Continuation of application No. 16/599,892, filed on Oct. 11, 2019, now Pat. No. 11,053,276, which is a continuation of application No. 15/728,459, filed on Oct. 9, 2017, now Pat. No. 10,487,109, which is a continuation of application No. 14/911,807, filed as application No. PCT/US2014/050565 on Aug. 11, 2014, now Pat. No. 9,802,978.

(60) Provisional application No. 61/864,681, filed on Aug. 12, 2013.

(51) Int. Cl.
| | |
|---|---|
| *C07J 41/00* | (2006.01) |
| *A61K 31/57* | (2006.01) |
| *C07J 51/00* | (2006.01) |
| *A61K 45/06* | (2006.01) |
| *A61K 31/661* | (2006.01) |
| *C07J 43/00* | (2006.01) |
| *A61K 31/58* | (2006.01) |

(52) U.S. Cl.
CPC ........... *C07J 41/0016* (2013.01); *A61K 31/57* (2013.01); *A61K 31/58* (2013.01); *A61K 31/661* (2013.01); *A61K 45/06* (2013.01); *C07J 41/005* (2013.01); *C07J 43/003* (2013.01); *C07J 51/00* (2013.01); *Y02A 50/30* (2018.01)

(58) Field of Classification Search
CPC ...... C07J 41/005; C07J 41/0016; C07J 51/00; A61K 31/57; A61P 25/00
See application file for complete search history.

(56) References Cited

U.S. PATENT DOCUMENTS

| | | | |
|---|---|---|---|
| 6,245,757 B1 | 6/2001 | Chopp et al. | |
| 6,331,534 B1 | 12/2001 | Berliner et al. | |
| 8,614,203 B2 | 12/2013 | Stein et al. | |
| 8,778,915 B2 | 7/2014 | Stein et al. | |
| 9,527,881 B2 | 12/2016 | Macnevin et al. | |
| 9,802,978 B2 | 10/2017 | Guthrie et al. | |
| 10,487,109 B2 | 11/2019 | Guthrie et al. | |
| 11,053,276 B2 | 7/2021 | Guthrie et al. | |
| 2006/0217358 A1 | 9/2006 | Bordet et al. | |
| 2011/0263553 A1 | 10/2011 | Macnevin et al. | |
| 2011/0306579 A1 | 12/2011 | Stein | |
| 2013/0210785 A1 | 8/2013 | Guthrie et al. | |
| 2016/0052957 A1 | 2/2016 | Guthrie et al. | |

FOREIGN PATENT DOCUMENTS

| | | |
|---|---|---|
| FR | 2238476 | 2/1975 |
| WO | 2009108804 | 9/2009 |

OTHER PUBLICATIONS

Application No. EP 21186868.2, Extended European Search Report, dated Mar. 1, 2022, 14 pages.
U.S. Appl. No. 15/728,459, Final Office Action, dated Jan. 15, 2019, 10 pages.
U.S. Appl. No. 15/728,459, Non Final Office Action, dated Apr. 11, 2018, 48 pages.
U.S. Appl. No. 15/728,459, Notice of Allowance, dated Jul. 22, 2019, 5 pages.
U.S. Appl. No. 16/599,892, Non-Final Office Action, dated Dec. 14, 2020, 5 pages.
U.S. Appl. No. 16/599,892, Non-Final Office Action, dated Sep. 2, 2020, 5 pages.
U.S. Appl. No. 16/599,892, Notice of Allowance, dated Mar. 12, 2021, 5 pages.
Barbakadze et al., "Chemical Modification of Oximes with N-Protected Amino Acids", Tetrahedron, vol. 70, No. 40, Oct. 7, 2014, pp. 7181-7184.
Application No. EP14835820.3, Extended European Search Report, dated Feb. 10, 2017, 7 pages.
* Application No. EP14835820.3, Notice of Decision to Grant, dated Jul. 1, 2021, 2 pages.
Application No. EP14835820.3, Office Action, dated Nov. 5, 2019, 5 pages.
Application No. EP14835820.3, Office Action, dated Oct. 30, 2020, 5 pages.
Application No. EP14835820.3, Office Action, dated Feb. 8, 2018, 6 pages.
Guthrie et al., "Water-soluble Progesterone Analogues are Effective, Injectable Treatments in Animal Models of Traumatic Brain Injury", ACS Medicinal Chemistry Letters, vol. 3, No. 5, Mar. 15, 2012, pp. 362-366.
Huttunen et al., "Prodrugs-from Serendipity to Rational Design", Pharmacological Reviews, vol. 63, No. 3, Sep. 2011, pp. 750-771.

(Continued)

*Primary Examiner* — Barbara P Badio
(74) *Attorney, Agent, or Firm* — Kilpatrick Townsend & Stockton LLP

(57) ABSTRACT

This disclosure relates to progesterone phophate derivatives and uses related thereto. In certain embodiments, the disclosure relates to compounds disclosed herein and uses for managing inflammation such as those resulting from traumatic brain injury or stroke.

20 Claims, 3 Drawing Sheets

(56) References Cited

OTHER PUBLICATIONS

Macnevin et al., "Development and Screening of Water-Soluble Analogues of Progesterone and Allopregnanolone in Models of Brain Injury", Journal of Medicinal Chemistry, vol. 52, No. 19, Oct. 8, 2009, pp. 6012-6023.

Mantyla et al., "Design, Synthesis and in Vitro Evaluation of Novel Watersoluble Prodrugs of Buparvaquone", European Journal of Pharmaceutical Sciences, vol. 23, No. 2, Oct. 2004, pp. 151-158.

Wall et al., "Evaluating the Neurotherapeutic Potential of a Water-Soluble Progesterone Analog After Traumatic Brain Injury in Rats", Neuropharmacology, vol. 109, Oct. 2016, pp. 148-158.

PROGESTERONE PHOSPHATE ANALOGS AND USES RELATED THERETO

CROSS-REFERENCE TO RELATED APPLICATIONS

This application is a continuation of U.S. application Ser. No. 16/599,892 filed Oct. 11, 2019, which is a continuation of U.S. application Ser. No. 15/728,459 filed Oct. 9, 2017, now issued as U.S. Pat. No. 10,487,109 on Nov. 26, 2019, which is a continuation of U.S. application Ser. No. 14/911,807 filed Feb. 12, 2016, now issued as U.S. Pat. No. 9,802,978 on Oct. 31, 2017, which is the National Stage of International Application Number PCT/US2014/050565 filed Aug. 11, 2014, which claims priority to U.S. Provisional Application No. 61/864,681 filed Aug. 12, 2013. The entirety of each of these applications is hereby incorporated by reference for all purposes.

FIELD

This disclosure relates to progesterone phosphate derivatives and uses related thereto. In certain embodiments, the disclosure relates to compounds disclosed herein and uses for managing inflammation such as those resulting from traumatic brain injury or stroke.

BACKGROUND

Brain injuries, including traumatic brain injury (TBI) and stroke, affect well over 2 million Americans each year and are a significant health concern worldwide. Traumatic brain injuries result from a blow or jolt to the head or a penetrating head injury that disrupts the function of the brain, with severity ranging from "mild," i.e., a brief change in mental status or consciousness to "severe," i.e., an extended period of unconsciousness or amnesia after the injury. In contrast, strokes are a result of diseases that affect the blood vessels that supply blood to the brain. A stroke occurs when a blood vessel that brings oxygen and nutrients to the brain either bursts (hemorrhagic stroke) or is clogged by a blood clot or some other mass (ischemic stroke). The majority of strokes are ischemic, however hemorrhagic strokes typically result in more severe injuries.

Despite several decades of effort, scientists have not yet found a pharmacological agent that consistently improves outcomes after stroke or TBI (see Sauerland, S. et al., Lancet 2004, 364, 1291-1292; Brain Trauma Foundation, American Association of Neurological Surgeons, Joint Section on Neurotrauma and Critical Care. Guidelines for the management of severe head injury. J. Neurotrauma 1996, 13, 641-734).

After TBI or stroke, inflammation is a principle cause of secondary damage and long-term damage. Following insults to the central nervous system, a cascade of physiological events leads to neuronal loss including, for example, an inflammatory immune response and excitotoxicity resulting from disrupting the glutamate, acetylcholine, cholinergic, GABAA, and NMDA receptor systems. In these cases, a complex cascade of events leads to the delivery of blood-borne leucocytes to sites of injury to kill potential pathogens and promote tissue repair. However, the powerful inflammatory response has the capacity to cause damage to normal tissue, and dysregulation of the innate, or acquired immune response is involved in different pathologies.

In addition to TBI and stroke, inflammation is being recognized as a key component of a variety of nervous system disorders. It has long been known that certain diseases such as multiple sclerosis result from inflammation in the central nervous system, but it is only in recent years that it has been suggested that inflammation may significantly contribute to neurodegenerative disorders such as HIV-related dementia, Alzheimer's and prion diseases. It is now known that the resident macrophages of the central nervous system (CNS), the microglia, when activated may secrete molecules that cause neuronal dysfunction, or degeneration.

There is growing experimental evidence that progesterone, its metabolites and other gonadal steroids such as estrogen and possibly testosterone, are effective neuroprotective agents. Pre-clinical and clinical research demonstrates that the hormone progesterone is a potent neurosteroid that, acutely administered, can dramatically reduce cerebral edema, inflammation, tissue necrosis, and programmed cell death (see Djebaili, M. et al, J. Neurotrauma 2005, 22, 106-118; Pettus, E. H. et al, Brain Res. 2005, 1049, 112-119; Grossman, K. J. et al, Brain Res, 2004, 1008, 29-39; He, J. et al, Exp. Neurol 2004, 189, 404-412; He, J. et al, Restor. Neurol Neurosci. 2004, 22, 19-31; Djebaili, M. et al, J. Neuroscience 2004, 123, 349-359; Hoffman, S. W. et al, Academy of Emergency Medicine, 2001, 8, 496-497; and Wright, D. W. et al, J. Neurotrauma. 2001, 18, 901-909).

In vivo data has demonstrated progesterone's neuroprotective effects in injured nervous systems. For example, following a contusion injury, progesterone reduces the severity of post injury cerebral edema. The attenuation of edema by progesterone is accompanied by the sparing of neurons from secondary neuronal death and improvements in cognitive outcome (Roof et al. (1994) Experimental Neurology 129:64-69). Furthermore, following ischemic injury in rats, progesterone has been shown to reduce cell damage and neurological deficit (Jiang et al. (1996) Brain Research 735:101-107). A Phase II, single-center, controlled trial involving 100 moderate to severe TBI patients showed that 3 days of intravenous progesterone treatment reduced mortality by over 60% and significantly improved functional outcomes at 30 days post-injury (see Wright, D. A. et al., Ann. Emerg. Med. 2007, 49, 391).

PCT Publication WO 2002/30409 to Emory University provides methods for conferring a neuroprotective effect on a population of cells in a subject following a traumatic injury to the central nervous system by administration of a progestin or progestin metabolite following a traumatic brain injury.

PCT Publication WO 2006/102644 also to Emory University provides methods for the treatment or the prevention of neuronal damage in the CNS by tapered administration of a progestin or progestin metabolite following a traumatic or ischemic injury to the CNS to avoid withdrawal.

PCT Publication No. WO 2006/102596 to Emory University provides certain methods of treating a subject with a traumatic central nervous system injury, more particularly, a traumatic brain injury that include a therapy comprising a constant or a two-level dosing regime of progesterone.

PCT Publication No. WO 2009/108804 to Emory University provides certain methods of treating a subject with a traumatic central nervous system injury. It also discloses certain progesterone analogs.

Studies have indicated that progesterone may be useful in treating or preventing neurodegeneration following stroke (see Stein, D. (2005) The Case for Progesterone US Ann. N. Y. Acad. ScL. 1052:152-169; Murphy, et al. (2002) Progesterone Administration During Reperfusion, But Not Preischemia Alone, Reduces Injury in Ovariectomized Rats. J.

Cereb. Blood Flow & Metab. 22:1181-1188; Murphy, et al. (2000) Progesterone Exacerbates Striatal Stroke Injury in Progesterone-Deficient Female Animals. Stroke 31: 1173).

U.S. Pat. No. 6,245,757, now expired, to Research Corporation Technologies, Inc. provides a method for the treatment of ischemic damage, such as damage due to stroke or myocardial infarction comprising administering to a mammal afflicted with stroke an effective amount of a neuroprotective steroid in a suitable vehicle.

In addition to being a gonadal steroid, progesterone also belongs to a family of autocrine/paracrine hormones called neurosteroids. Neurosteroids are steroids that accumulate in the brain independently of endocrine sources and which can be synthesized from sterol precursors in nervous cells. These neurosteroids can potentiate GABA transmission, modulate the effects of glutamate, enhance the production of myelin, and prevent release of free radicals from activated microglia.

Various metabolites of progesterone have also been thought to have neuroprotective properties. For instance, the progesterone metabolites allopregnanolone or epipregnanolone are positive modulators of the GABA receptor, increasing the effects of GABA in a manner that is independent of the benzodiazepines (Baulieu, E. E. (1992) Adv. Biochem. Psychopharmacol. 47:1-16; Robel et al. (1995) Crit. Rev. Neurobiol. 9:383-94; Lambert et al. (1995) Trends Pharmacol. ScL 16:295-303; Baulieu, E. E. (1997) Recent Prog. Horm. Res. 52:1-32; Reddy et al. (1996) Psychopharmacology 128:280-92). In addition, these neurosteroids act as antagonists at the sigma receptor, which can activate the NMDA channel complex (Maurice et al. (1998) Neuroscience 83:413-28; Maurice et al. (1996) J. Neurosci. Res. Aβ:1M-A7>; Reddy et al. (1998) Neuroreport 9:3069-73). These neurosteroids have also been shown to reduce the stimulation of cholinergic neurons and the subsequent release of acetylcholine by excitability. Numerous studies have shown that the cholinergic neurons of the basal forebrain are sensitive to injury and that excessive release of acetylcholine can be more excitotoxic than glutamate (Lyeth et al. (1992) J. Neurotrauma 9(2):S463-74; Hayes et al. (1992) J. Neurotrauma 9(1):S173-87).

As discussed above, following a traumatic injury to the central nervous system, a cascade of physiological events leads to neuronal loss. In addition, the injury is frequently followed by brain and/or spinal cord edema that enhances the cascade of injury and leads to further secondary cell death and increased patient mortality. Methods are needed for the in vivo treatment of traumatic CNS injuries that are successful at providing subsequent trophic support to remaining central nervous system tissue, and thus enhancing functional repair and recovery, under the complex physiological cascade of events which follow the initial insult.

TBI produces a complex succession of molecular events in addition to the immediate loss of nervous tissue caused by concussions, contusions and ballistic injuries. The "brain injury cascade" initiates rapidly after the initial trauma and unfolds over days, weeks and even months. Therefore, an important tenet of brain injury treatment is that the sooner one can treat/prevent edema, inflammation and neuronal loss, the better the functional outcome will be. Current clinical protocols for the use of progesterone occur once patients are transported to a hospital setting, thus losing valuable time before the treatment can be administered. As a natural product, progesterone is insoluble in aqueous-based formulations, and is typically delivered in a freshly prepared lipid formulation, a fairly complicated and time-consuming preparation. Furthermore, the plasma half-life of progesterone is limited, so treatment typically institutes a continuous i.v. drip, or multiple injections with an oil-based formulation delaying release to the systemic circulation. Thus there is a need for an improved treatment for TBI that can be administered easily and rapidly.

US Patent Application Publication number, US20130210785 reports progesterone analogues.

References cited herein are not an admission of prior art.

SUMMARY

This disclosure relates to progesterone phosphate derivatives and uses related thereto. In certain embodiments, the disclosure relates to compounds disclosed herein and uses for managing inflammation such as those resulting from traumatic brain injury or stroke. In certain embodiments, the disclosure relates to compounds of Formula I

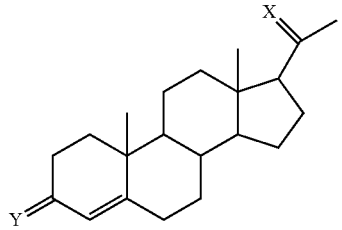

Formula I or esters, prodrugs, or salts thereof wherein

X is O, N—$OR^{10}$, or N—$OCR^1R^2OPZ(OR^3)_2$;

Y is O, N—$OR^{10}$, or N—$OCR^1R^2OPZ(OR^3)_2$; provided at least one X or Y is N—$OCR^1R^2OPO(OR^3)_2$;

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

each $R^3$ is independently and individually phosphate ion, hydrogen, —$CH_2O(C=O)$alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is hydrogen or a group selected from alkyl and formyl further substituted with one or more, the same or different, alkyl, amino, hydroxyl, thiol, halogen, aryl, carbocyclyl, or heterocyclyl, wherein $R^{10}$ is optionally substituted with one or more, the same or different, $R^{20}$;

$R^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{30}$;

$R^{30}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{40}$; and $R^{40}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to pharmaceutical compositions comprising a compound disclosed herein and a pharmaceutically acceptable excipient. The pharmaceutical composition may optionally further comprise a second active therapeutic agent.

In certain embodiments, the disclosure relates to methods of treating or preventing inflammation comprising administering an effective amount of a compound or a pharmaceutical composition comprising a compound disclosed herein to a subject in need thereof. In certain embodiments, the pharmaceutical composition is administered to a subject that incurred trauma to the head or other organ or tissue. In certain embodiments, the pharmaceutical composition is administered after a medical procedure. In certain embodiments, the pharmaceutical composition is administered in combination with a second anti-inflammatory agent.

In certain embodiments, the disclosure relates to methods of treating stroke or traumatic brain injury comprising administering an effective amount of a compound or a pharmaceutical composition comprising a compound disclosed herein to a subject in need thereof.

In other embodiments, the disclosure relates to methods of treating or preventing neurodegeneration resulting from ischemic CNS injuries, in particular from ischemic stroke comprising administering a compound disclosed herein to a patient in need thereof.

In yet other embodiments, the disclosure relates to methods of treating or preventing neurodegeneration resulting from hemorrhagic CNS injuries, in particular from hemorrhagic stroke comprising administering a compound disclosed herein to a patient in need thereof. The methods can alleviate the initial damage to the CNS. Therefore, in some embodiments, the compounds are administered to a patient at risk of a CNS injury, in particular to a patient at risk of a stroke. The compounds are also effective at reducing or preventing secondary injuries. Therefore, in other embodiments, the compounds are administered to a patient who has suffered a CNS injury within a window of opportunity after the initial insult. The initial insult can be either a TBI or a stroke, whether that be an ischemic or hemorrhagic stroke.

In certain embodiments, the disclosure relates to methods of treating or preventing a neurodegenerative disease or condition comprising administering an effective amount of a pharmaceutical composition to a subject in need thereof, e.g., at risk of, exhibiting symptoms of, or diagnosed with the disease or condition. Contemplated neurodegenerative diseases or conditions include, but are not limited to, Alzheimer's disease, Parkinson's disease, Huntington's disease, multiple sclerosis, amyotrophic lateral sclerosis, dementia, extrapyramidal and movement disorders, motor neurone disease, systemic atrophies primarily affecting the central nervous system, Tay-Sachs disease, ataxia telangiectasia, Batten disease, corticobasal degeneration, Creutzfeldt-Jakob disease, fatal familial insomnia, infantile Refsum disease, lyme disease, Machado-Joseph disease, multiple system atrophy, neuroacanthocytosis, Niemann-Pick disease, refsum disease, Sandhoff disease, Shy-Drager syndrome, spinocerebellar ataxia, tabes dorsalis, toxic encephalopathy, and Wobbly hedgehog syndrome.

Pharmaceutical compositions, including in combination with additional neuroprotective agents, are also provided.

In certain embodiments, the disclosure relates to the production of a medicament for uses disclosed herein.

In certain embodiments, the disclosure relates to methods of making compounds disclosed herein comprising mixing starting materials disclosed herein to form compounds disclosed herein.

In certain embodiment, the disclosure relates to compounds disclosed herein and derivatives such as the compounds substituted with one or more substituents and salts thereof.

DETAILED DESCRIPTION

Figure 1:
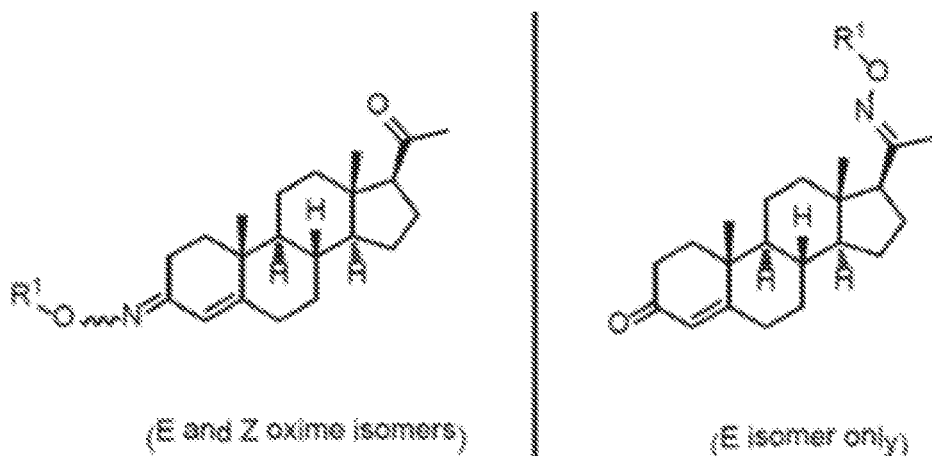
FIG. 1 illustrates certain embodiments of the disclosure. $R^2$=H, methyl, ethyl; $R^3$=H, methyl, ethyl; or $R^2$ and $R^3$ together=methylene groups bonded to one another forming a cyclopropyl ring: —H$_2$C—CH$_2$—; X=H, Li$^+$, Na$^+$, K$^+$, trialkylammonium or other pharmaceutically acceptable cations with +1 charge; Y=H, Li$^+$, Na$^+$, K$^+$, trialkylammonium or other pharmaceutically acceptable cations with +1 charge; or X and Y together=Ca$^{2+}$, Mg$^{2+}$, or other pharmaceutically acceptable cations with +2 charge.
Figure 1:
Figure 2:
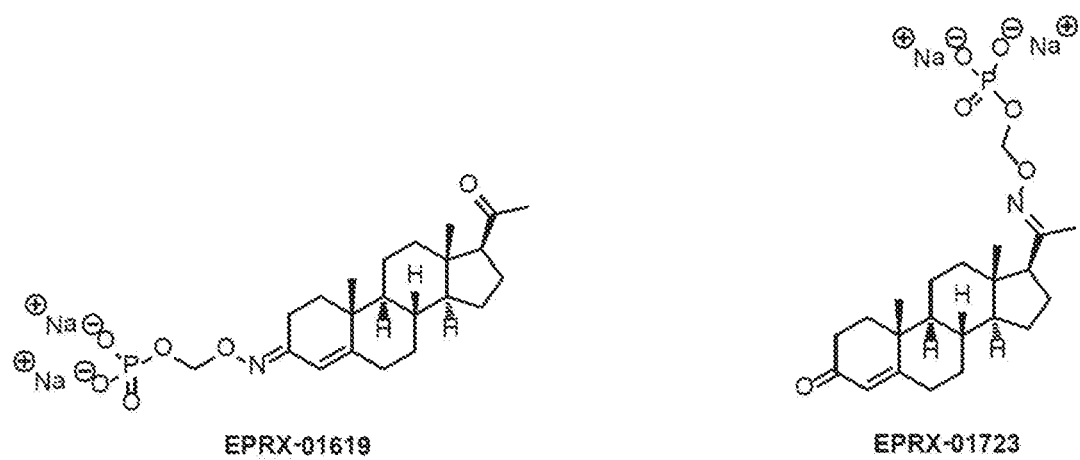
FIG. 2 illustrated certain embodiments of the disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated. As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), mono-cyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH₃).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above attached through an amino bridge. An example of an alkylamino is methylamino, (i.e., —NH—CH₃).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)₂alkyl) such as mesyl and the like, and "Arylsulfonyl" refers to an aryl attached through a sulfonyl bridge (i.e., —S(=O)₂aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids and phosphates; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. In certain embodiments, the compounds herein are phosphate salts with a positive one or two metal cation such as sodium, lithium, potassium, quaternary ammonium, calcium, magnesium, or combinations thereof.

"Subject" refers any animal, preferably a human patient, livestock, rodent, primate, monkey, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

PROG, Progesterone; TBI, traumatic brain injury; EDCI, N-(3-Dimethylaminopropyl)-N'-ethylcarbodiimide hydrochloride; DMAP, 4-dimethylaminopyridine.

Compounds

In certain embodiments, the disclosure relates to compounds of Formula I

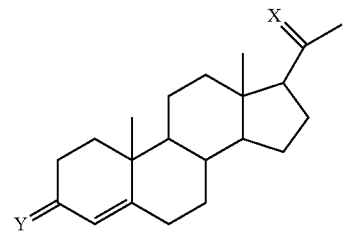

Formula I or esters, prodrugs, or salts thereof wherein
X is O, N—OR$^{10}$, or N—OCR$^1$R$^2$OPZ(OR$^3$)$_2$;
Y is O, N—OR$^{10}$, or N—OCR$^1$R$^2$OPZ(OR$^3$)$_2$; provided at least one X or Y is N—OCR$^1$R$^2$OPO(OR$^3$)$_2$;
Z is =O or =S;
R$^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^4$;
R$^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^2$ is optionally substituted with one or more, the same or different, R$^4$; or
R$^1$ and R$^2$ form a carbocyclic ring;
each R$^3$ is independently and individually individually phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is hydrogen or a group selected from alkyl and formyl further substituted with one or more, the same or different, alkyl, amino, hydroxyl, thiol, halogen, aryl, carbocyclyl, or heterocyclyl, wherein $R^{10}$ is optionally substituted with one or more, the same or different, $R^{20}$;

$R^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{30}$;

$R^{30}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{40}$; and $R^{40}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is N—OCR$^1$R$^2$OPZ(OR$^3$)$_2$ and Y is O or N—OR$^{10}$.

In certain embodiments, Y is N—OCR$^1$R$^2$OPZ(OR$^3$)$_2$ and X is O or N—OR$^{10}$.

In certain embodiments, $R^1$ and $R^2$ are hydrogen or alkyl.

In certain embodiments, $R^1$ and $R^2$ form a cyclopropyl ring.

In certain embodiments, $R^3$ is phosphate ion, hydrogen, alkanoyl, or alkyl, wherein $R^3$ is optionally substituted with one or more, the same or different, $R^4$;

In certain embodiments, the compounds are phosphate salts with a positive one or two metal cation such as sodium, lithium, potassium, quaternary ammonium, calcium, magnesium, or combinations thereof.

In certain embodiments, the disclosure relates to compounds of formula I having formula IA

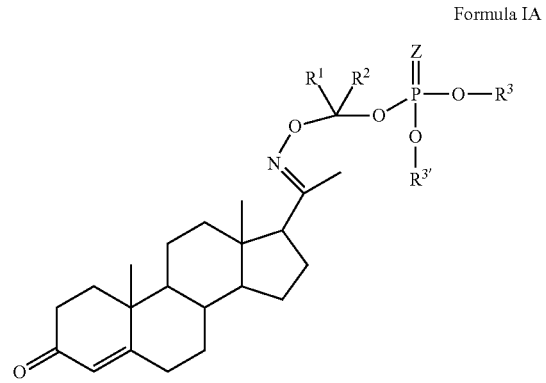

Formula IA or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of Formula IB

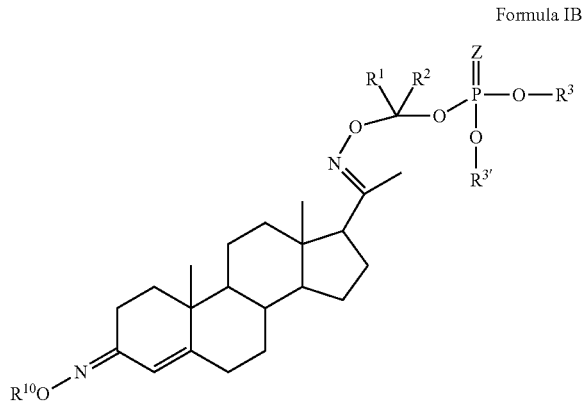

Formula IB or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is hydrogen or a group selected from alkyl and formyl substituted with one or more, the same or different, alkyl, amino, hydroxyl, thiol, halogen, aryl, carbocyclyl, or heterocyclyl, wherein $R^{10}$ is optionally substituted with one or more, the same or different, $R^{20}$;

$R^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{30}$;

$R^{30}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{40}$; and $R^{40}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of formula I having Formula IC

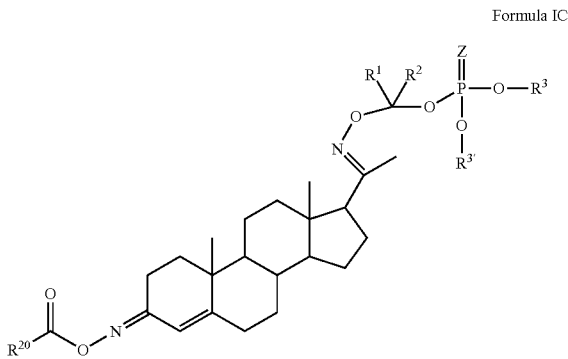

Formula IC or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{20}$ is alkyl, alkoxy, alkylthio, alkylamino, (alkyl)$_2$amino, carbocyclyl, aryl, or heterocyclyl, wherein $R^{20}$ is optionally substituted with one or more, the same or different, $R^{30}$;

$R^{30}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^4$; and $R^{40}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of formula IC, wherein $R^{20}$ is heterocyclyl or alkyl substituted with a group selected from amino and heterocyclyl, wherein $R^{20}$ is optionally substituted with one or more, the same or different, $R^{30}$.

In certain embodiments, the disclosure relates to compounds of formula I having Formula ID

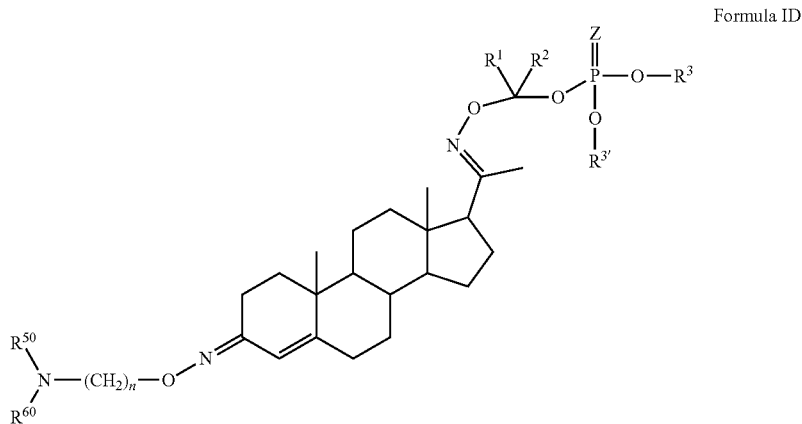

Formula ID or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

n is 1, 2, 3, or 4;

$R^{50}$ and $R^{60}$ and the attached nitrogen form a 5 or 6 membered heterocyclyl optionally substituted with one or more, the same or different, $R^{70}$; or $R^{50}$ is alkyl, alkoxy, alkylthio, alkylamino, (alkyl)$_2$amino, carbocyclyl, aryl, or heterocyclyl, wherein $R^5$ is optionally substituted with one or more, the same or different, $R^{70}$;

$R^{60}$ is alkyl, alkoxy, alkylthio, alkylamino, (alkyl)$_2$amino, carbocyclyl, aryl, or heterocyclyl, wherein $R^{60}$ is optionally substituted with one or more, the same or different, $R^{70}$;

$R^{70}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{70}$ is optionally substituted with one or more, the same or different, $R^{80}$; and $R^{80}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of formula I having Formula IE alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, Formula IE

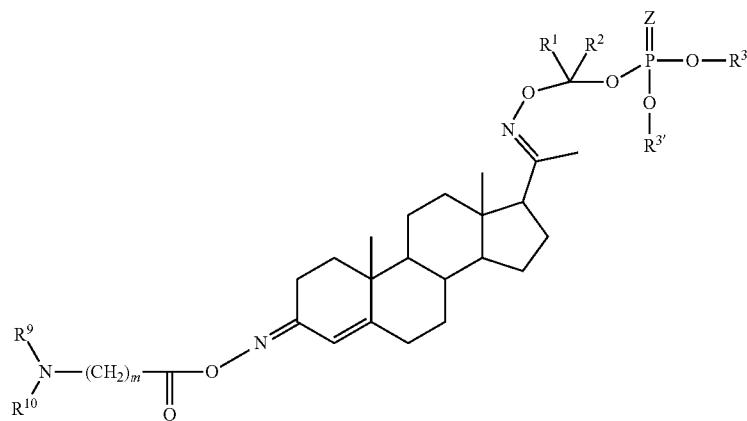

or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

m is 1, 2, 3, or 4;

$R^9$ and $R^{10}$ and the attached nitrogen form a 5 or 6 membered heterocyclyl optionally substituted with one or more, the same or different, $R^{11}$; or $R^9$ is alkyl, alkoxy, alkylthio, alkylamino, (alkyl)$_2$amino, carbocyclyl, aryl, or heterocyclyl, wherein $R^9$ is optionally substituted with one or more, the same or different, $R^{11}$;

$R^{10}$ is alkyl, alkoxy, alkylthio, alkylamino, (alkyl)$_2$amino, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, m is 0 or 1.

In certain embodiments, m is 2 or 3.

In certain embodiments, $R^9$ and $R^{10}$ is morpholinyl, pyrrolidinyl, piperidinyl, or piperazinyl ring optionally substituted with one or more, the same or different, $R^{11}$.

In certain embodiments, $R^9$ and $R^{10}$ is morpholinyl, pyrrolidinyl, piperidinyl, or piperazinyl ring further substituted with one or more, the same or different, $R^{11}$.

In certain embodiments, the disclosure relates to compounds of formula I having Formula IF $R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

Formula IF

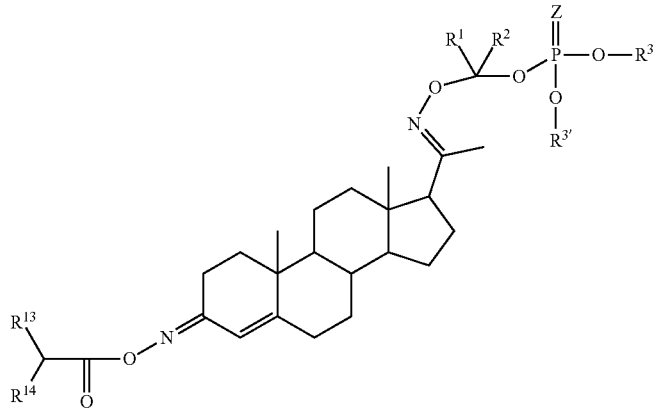

or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^{13}$ and $R^{14}$ are the same or different alkyl optionally substituted with one or more, the same or different, $R^{15}$; or $R^{13}$ and $R^{14}$ and the attached carbon form a 5 or 6 membered aryl or heterocyclyl optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{13}$ and $R^{14}$ is morpholinyl, piperidinyl, or piperazinyl ring optionally substituted with one or more, the same or different, $R^{15}$.

In certain embodiments, $R^{13}$ and $R^{14}$ is morpholinyl, pyrrolidinyl, piperidinyl, or piperazinyl ring further substituted with one or more, the same or different, $R^{15}$.

In certain embodiments, $R^{13}$ and $R^{14}$ is an aromatic heterocyclyl such as pyridinyl In certain embodiments, the disclosure relates to compounds of formula I having Formula IG

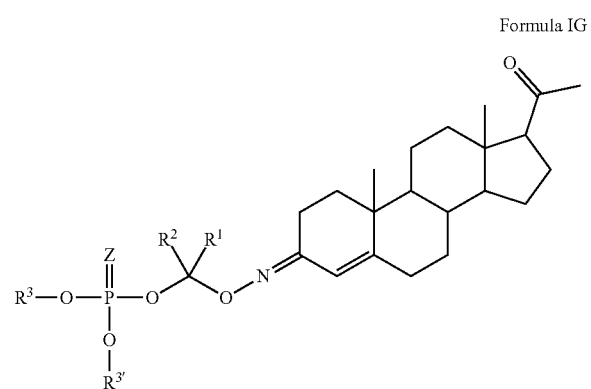

Formula IG or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the oxime composition is in greater than 60, 70, 80, 90, or 95% of the E or Z configuration. Certain embodiments are exemplified below.

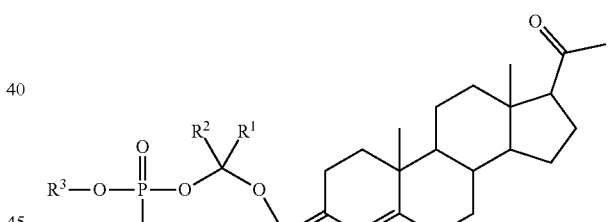

E-oxime

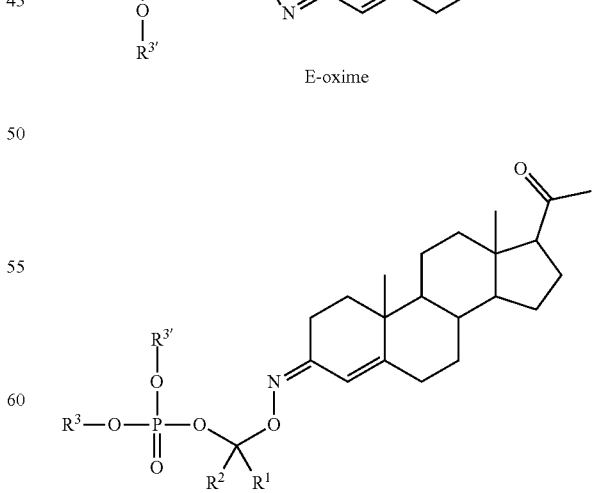

Z-oxime

In certain embodiments, the disclosure relates to compounds of formula I having Formula IH

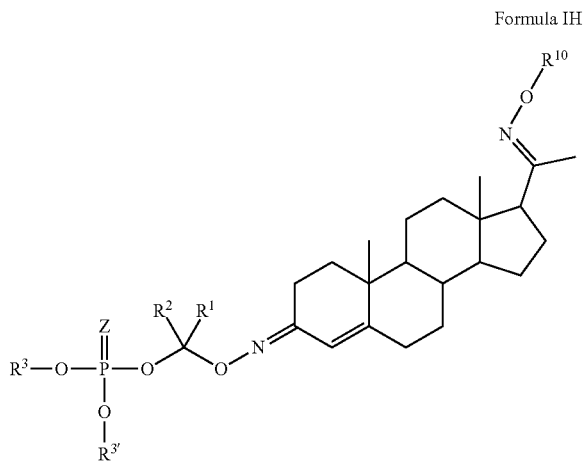

Formula IH or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is hydrogen or a group selected from alkyl and formyl substituted with one or more, the same or different, alkyl, amino, hydroxyl, thiol, halogen, aryl, carbocyclyl, or heterocyclyl, wherein $R^{10}$ is optionally substituted with one or more, the same or different, $R^{20}$;

$R^{20}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{30}$;

$R^{30}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{40}$; and $R^{40}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of formula I having Formula II

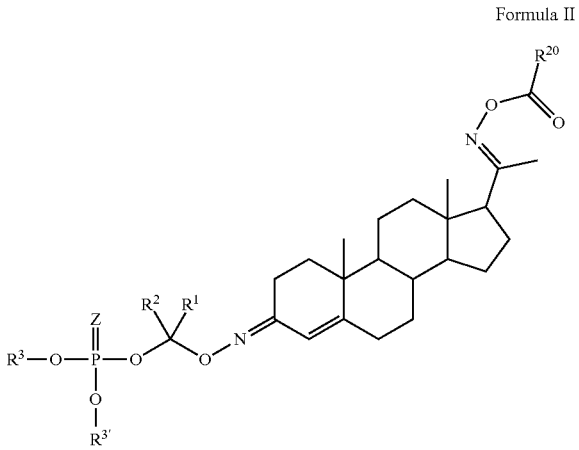

Formula II or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

R³ is phosphate ion, hydrogen, —CH₂O(C═O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein R³ is optionally substituted with one or more, the same or different, R⁴;

R³ is phosphate ion, hydrogen, —CH₂O(C═O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein R³⁰ is optionally substituted with one or more, the same or different, R⁴;

R⁴ is alkyl, halogen, nitro, cyano, hydroxy, amino, mercapto, formyl, carboxy, alkanoyl, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R⁵; and R⁵ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

R²⁰ is alkyl, alkoxy, alkylthio, alkylamino, (alkyl)₂amino, carbocyclyl, aryl, or heterocyclyl, wherein R²⁰ is optionally substituted with one or more, the same or different, R³⁰;

R³⁰ is alkyl, halogen, nitro, cyano, hydroxy, amino, mercapto, formyl, carboxy, alkanoyl, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R³⁰ is optionally substituted with one or more, the same or different, R⁴⁰; and R⁴⁰ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of formula II, wherein R²⁰ is heterocyclyl or alkyl substituted with a group selected from amino and heterocyclyl, wherein R²⁰ is optionally substituted with one or more, the same or different, R³⁰.

In certain embodiments, the disclosure relates to compounds of formula I having Formula IJ

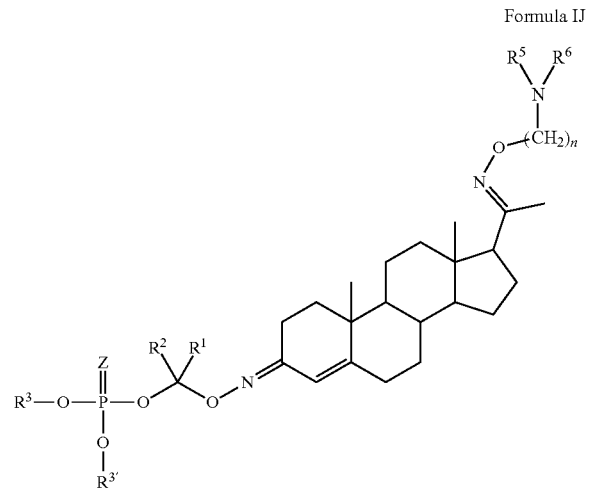

Formula IJ or esters, prodrugs, or salts thereof wherein

Z is ═O or ═S;

R¹ is hydrogen, alkyl, halogen, nitro, cyano, hydroxy, amino, mercapto, formyl, carboxy, alkanoyl, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹ is optionally substituted with one or more, the same or different, R⁴;

R² is hydrogen, alkyl, halogen, nitro, cyano, hydroxy, amino, mercapto, formyl, carboxy, alkanoyl, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R² is optionally substituted with one or more, the same or different, R⁴; or R¹ and R² form a carbocyclic ring;

R³ is phosphate ion, hydrogen, —CH₂O(C═O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein R³ is optionally substituted with one or more, the same or different, R⁴;

R³' is phosphate ion, hydrogen, —CH₂O(C═O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein R³' is optionally substituted with one or more, the same or different, R⁴;

R⁴ is alkyl, halogen, nitro, cyano, hydroxy, amino, mercapto, formyl, carboxy, alkanoyl, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R⁴ is optionally substituted with one or more, the same or different, R⁵; and R⁵ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

n is 1, 2, 3, or 4;

$R^{50}$ and $R^{60}$ and the attached nitrogen form a 5 or 6 membered heterocyclyl optionally substituted with one or more, the same or different, $R^{70}$; or $R^{50}$ is alkyl, alkoxy, alkylthio, alkylamino, (alkyl)$_2$amino, carbocyclyl, aryl, or heterocyclyl, wherein $R^{50}$ is optionally substituted with one or more, the same or different, $R^{70}$;

$R^{60}$ is alkyl, alkoxy, alkylthio, alkylamino, (alkyl)$_2$amino, carbocyclyl, aryl, or heterocyclyl, wherein $R^{60}$ is optionally substituted with one or more, the same or different, $R^{70}$;

$R^{70}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{70}$ is optionally substituted with one or more, the same or different, $R^{80}$; and $R^{80}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 1.

In certain embodiments, n is 2 or 3.

In certain embodiments, $R^{50}$ and $R^{60}$ is morpholinyl, pyrrolidinyl, piperidinyl, or piperazinyl ring optionally substituted with one or more, the same or different, $R^{70}$.

In certain embodiments, the disclosure relates to compounds of formula I having Formula IK

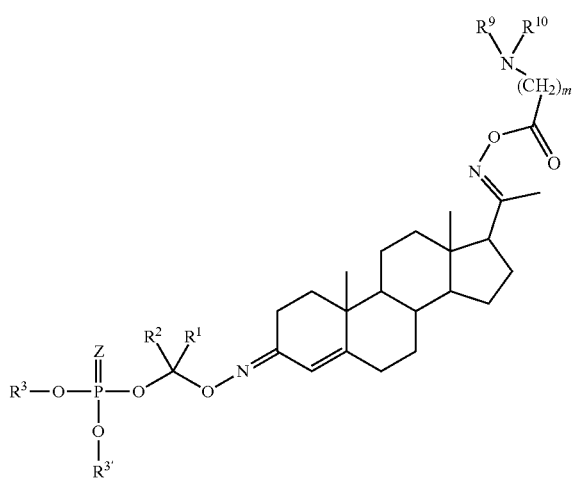

Formula IK or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

m is 1, 2, 3, or 4;

$R^9$ and $R^{10}$ and the attached nitrogen form a 5 or 6 membered heterocyclyl optionally substituted with one or more, the same or different, $R^{11}$; or $R^9$ is alkyl, alkoxy, alkylthio, alkylamino, (alkyl)$_2$amino, carbocyclyl, aryl, or heterocyclyl, wherein $R^9$ is optionally substituted with one or more, the same or different, $R^{11}$;

$R^{10}$ is alkyl, alkoxy, alkylthio, alkylamino, (alkyl)$_2$amino, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, m is 0 or 1.

In certain embodiments, m is 2 or 3.

In certain embodiments, $R^9$ and $R^{10}$ is morpholinyl, pyrrolidinyl, piperidinyl, or piperazinyl ring optionally substituted with one or more, the same or different, $R^{11}$.

In certain embodiments, $R^9$ and $R^{10}$ is morpholinyl, pyrrolidinyl, piperidinyl, or piperazinyl ring further substituted with one or more, the same or different, $R^{11}$.

In certain embodiments, the disclosure relates to compounds of formula I having Formula IL Formula IL

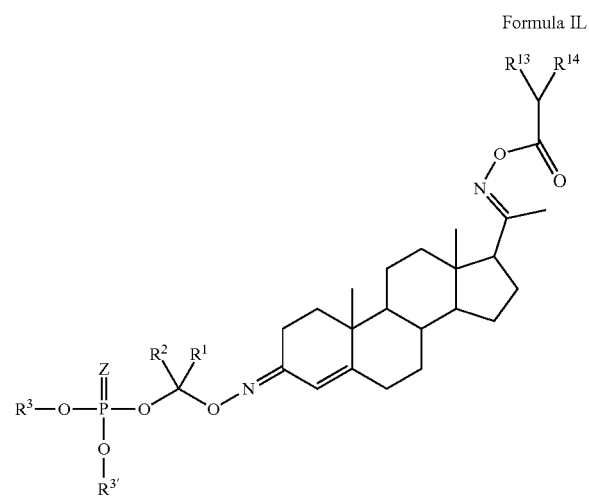

or esters, prodrugs, or salts thereof wherein

Z is =O or =S;

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^4$;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^4$; or $R^1$ and $R^2$ form a carbocyclic ring;

$R^3$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^3$ is optionally substituted with one or more, the same or different, $R^4$;

$R^{3'}$ is phosphate ion, hydrogen, —CH$_2$O(C=O)alkyl, or a group selected from alkyl, alkanoyl, and formyl further substituted with one or more, the same or different, alkyl, amino, hydroxyl, thiol, halogen, aryl, carbocyclyl, or heterocyclyl, wherein $R^{3'}$ is optionally substituted with one or more, the same or different, $R^4$;

$R^4$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$; and $R^5$ is halogen, nitro, cyano, hydroxy, trifluoromethoxy, trifluoromethyl, amino, formyl, carboxy, carbamoyl, mercapto, sulfamoyl, methyl, ethyl, tertbutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{13}$ and $R^{14}$ are the same or different alkyl optionally substituted with one or more, the same or different, $R^{15}$; or $R^{13}$ and $R^{14}$ and the attached carbon form a 5 or 6 membered aryl or heterocyclyl optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Methods of Use

Treatment of CNS Damage

In certain embodiments, the disclosure relates to methods and compositions for the treatment or prevention of neurodegeneration following an injury to the central nervous system or due to certain neurodegenerative disorders comprising administering an effective amount of a compound described herein, or a pharmaceutically acceptable salt, ester or prodrug thereof to a subject in need thereof. Multiple physiological events lead to neurodegeneration. These events include, for example, increase in the immune and inflammatory response, demyelinization, and lipid peroxidation. In certain embodiments, the disclosure relates to compositions and methods for reducing or eliminating neuronal cell death, edema, ischemia, and enhancing tissue viability following injury to the central nervous system or certain disorders. The analogues, salts, esters or prodrugs of the, compound, steroid, or secosteroid analogs may be optionally administered with a pharmaceutically acceptable carrier or diluent.

As used herein, "neuroprotection" is the prevention, arrest or reverse progression of neurodegeneration following a central nervous system injury. The neuroprotective effect includes both improved morphological (i.e., enhanced tissue viability) and/or behavioral recovery. CNS injuries that are encompassed within the scope of treatment include both traumatic injuries, in particular TBI, and physiological insults such as an ischemic or hemorrhagic stroke. In both instances, a progressive loss of neurons after the initial insult occurs and can be alleviated.

In certain embodiments, the disclosure relates to methods of preventing or reducing inflammatory reactions in a patient by administering a compound disclosed herein to a subject in need thereof. In certain embodiments, methods of neuroprotection are provided comprising administering a compound disclosed herein, its physiologically acceptable salt or prodrug, optionally in a pharmaceutically acceptable carrier, to a patient at risk of suffering from a stroke. In other embodiments, methods of treating or preventing neuronal damage are provided comprising administering a compound disclosed herein or its physiologically acceptable salt or prodrug, optionally in a pharmaceutically acceptable carrier, to a patient who has suffered from an ischemic stroke. The method can reduce or prevent neurodegeneration such as that caused by excitotoxic or inflammatory reactions, or can enhance neuronal proliferation, growth or differentiation in the period after the injury. In yet further embodiments, methods of treating or preventing cognitive or behavioral deficits after a stroke is provided comprising administering a compound disclosed herein or its physiologically acceptable salt or prodrug, optionally in a pharmaceutically acceptable carrier, to a human subject who has suffered a stroke. In certain embodiments, the stroke is an ischemic stroke, but it can alternatively be a hemorrhagic stroke.

In other embodiments, the present disclosure relates to methods to achieve a neuroprotective effect following a traumatic CNS injury in a mammal, in particular in a human, comprising administering a therapeutically effective amount of a compound disclosed herein. A traumatic injury to the CNS is characterized by a physical impact to the central nervous system. The physical forces resulting in a traumatic brain injury cause their effects by inducing three types of injury: skull fracture, parenchymal injury, and vascular injury. A blow to the surface of the brain typically leads to rapid tissue displacement, disruption of vascular channels, and subsequent hemorrhage, tissue injury and edema. Morphological evidence of injury in the neuronal cell body includes pyknosis of nucleus, eosinophilia of the cytoplasm, and disintegration of the cell. Furthermore, axonal swelling can develop in the vicinity of damage neurons and also at great distances away from the site of impact.

In certain embodiments, the compound is administered within twelve hours after onset of a stroke. In certain embodiments, the compound is administered within twelve hours after an injury, such as a TBI. In some embodiments, the compound is administered within 11 hours of a TBI, stroke or other injury to the brain, or within 10 hours, or within 9 hours, or within 8 hours, or within 7 hours, or within 6 hours, or within 5 hours, or within 4 hours, or within 3 hours, such as within two or one hour. In some embodiments, the compounds are administered within one day (i.e. 24 hours) of the injury. In certain embodiments, the compounds are provided to individuals at risk of a stroke, such as those who are suffering from atherosclerosis or have a family history of heart disease. These compounds can be provided to individuals as a preventative therapy to decrease neural trauma.

In another embodiment, a method for decreasing ischemia following a brain injury is provided comprising administering an effective amount of a compound disclosed herein. Although it is not intended that embodiments of the disclosure work by any particular mechanism, it is believed that administering certain compound is a means to reduce or eliminate the inflammatory immune reactions that follow a CNS injury. By reducing the inflammatory response, the compounds can substantially reduce brain swelling and reduce the amount of neurotoxic substances (e.g., free radicals and excitotoxins) that are released from the site of injury.

In certain embodiments, the concentration of the compound or salt, ester or prodrug thereof, is effective in the treatment or prevention of typical neuronal damage that follows either a traumatic, ischemic or hemorrhagic injury to the CNS and hence, elicits a neuroprotective effect. The therapeutically effective amount will depend on many factors including, for example, the specific activity of the compound administered, the type of injury, the severity and pattern of the injury, the resulting neuronal damage, the responsiveness of the patient, the weight of the patient along with other intraperson variability, the method of administration, and the formulation used.

It is recognized that a traumatic injury to the CNS results in multiple physiological events that impact the extent and rate of neurodegeneration, and thus the final clinical outcome of the injury. The treatment of a traumatic injury to the CNS encompasses any reduction and/or prevention in one or more of the various physiological events that follow the initial impact. For example, cerebral edema frequently develops following a traumatic injury to the CNS and is a leading cause of death and disability. Cortical contusions, for example, produce massive increases in brain tissue water content which, in turn, can cause increased intracranial pressure leading to reduced cerebral blood flow and additional neuronal loss. Hence, the methods disclosed herein find use in reducing and/or eliminating cerebral edema and/or reducing the duration of the edemic event following a traumatic injury to the CNS. Assays to determine a reduction in edema are known in the art and include, but are not limited to, a decrease in tissue water content following the administration of the progestin or the progestin metabolite (Betz et al. (1990) Stroke 21: 1199-204, which is herein incorporated by reference). Furthermore, an overall improvement in behavioral recovery can also be used as a measure for a decrease in edema. A decrease in edema in the effected tissue by at least about 15% to 30%, about 30% to 45%, about 45% to 60%, about 60% to 80%, or about 80% to 95% or greater will be therapeutically beneficial, as will any reduction in the duration of the edemic event.

Further physiological effects of brain injury include an inflammatory response. In particular, some studies indicate that the acute inflammatory response contributes significantly to injury after ischemia (see Perera, et al. (2005) Inflammation following stroke. J. CHn. Neurosc. 13:1-8; Barone and Feuerstein (1999) Inflammatory mediators and stroke: new opportunities for novel therapeutics). The stroke process triggers an inflammatory reaction that may last up to several months. Suppression of inflammation can reduce infarct volume and improve clinical outcomes even with the initiation of therapy after 3 hours of onset of stroke. In addition, an immune response can be triggered both by strokes. Infiltrating leukocytes are thought to contribute to secondary ischemic damage by producing toxic substances that kill brain cells and disrupt the blood-brain barrier (see del Zoppo, et al. (2000) Advances in the vascular pathophysiology of ischemic stroke. Thromb Res. 98:73-81) Infiltration occurs when leukocytes bind endothelial intercellular adhesion molecule-1 (ICAM-I) and ICAM-I is upregulated after ischemia.

TBI also elicits inflammatory, and in particular an immune responses. See, for example, Soares et al. (1995) J. Neurosci. 15:8223-33; Holmin et al. (1995) Acta Neurochir. 132:110-9; Arvin et al. (1996) Neurosci. Biobehav. Rev. 20:445-52. Following a cortical impact, severe inflammatory reactions and gliosis at the impact site and at brain areas distal to the primary site of injury occurs. The inflammatory response is characterized by the expression of adhesion molecules on the vascular surfaces, resulting in the adherence of immune cells and subsequent extravasation into the brain parenchyma. By releasing cytokines, the invading macrophages and neutrophils stimulate reactive astrocytosis. Release of different chemokines by other cell types induces these immune cells to become phagocytic, with the simultaneous release of free radicals and pro-inflammatory compounds, e.g., cytokines, prostaglandins, and excitotoxins (Arvin et al. (1996) Neurosci. Biobehav. Ref. 20:445-52; Raivich et al. (1996) Kelo J. Med. 45:239-47; Mattson et al. (1997) Brain Res. Rev. 23:47-61; all of which are herein incorporated by reference).

Assays for assessing the efficacy of the compounds described herein include assays to determine a decrease in an ischemic event include, for example, a decrease in infarct area, improved body weight, and improved neurological outcome. Assays to measure a reduction in lipid peroxidation in both brain homogenate and in mitochondria are known in the art and include, for example, the thiobarbituric acid method (Roof et al. (1997) Mol. Chem. Neuropathol. 31: 1-11; Subramanian et al. (1993) Neurosci. Lett. 155: 151-4; Goodman et al. (1996) J. Neurochem. 66:1836-44; Vedder et al. (1999) J. Neurochem. 72:2531-8; all of which are herein incorporated by reference) and various in vitro free radical generating systems. Furthermore, alterations in the levels of critical free radical scavenger enzymes, such as mitochondrial glutathione can be assayed. See, for example, Subramanian et al. (1993) Neurosci. Lett. 155:151-4; and Vedder et al. (1999) J. Neurochem. 72:2531-8; both of which are herein incorporated by reference.

Methods to quantify the extent of central nervous system damage (i.e., neurodegeneration) and to determine if neuronal damage was treated or prevented following the administration of a progesterone or compound disclosed herein are well known in the art. Such neuroprotective effects can be assayed at various levels, including, for example, by promoting behavioral and morphological (i.e., enhancing tissue viability) recovery after traumatic brain injury. A variety of anatomical, immunocytochemical and immunological assays to determine the effect of the progestin metabolite on necrosis, apoptosis, and neuronal glial repair are known in the art. As such, the neuroprotection will typically result in at least about a 10% to 20%, 20% to 30%, 30% to 40%, 40% to 60%, 60% to 80% or greater increase in neuronal survival and/or behavioral recovery as compared to the control groups.

Histological and molecular marker assays for an increase in neuronal survival are known. For example, Growth Associated Protein 43 (GAP-43) can be used as a marker for new axonal growth following a CNS insult. See, for example, Stroemer et al. (1995) Stroke 26:2135-2144, Vaudano et al. (1995) J. of Neurosci 15:3594-3611. Other histological markers can include a decrease in astrogliosis and microgliosis. Alternatively, a delay in cellular death can be assayed using TUNEL labeling in injured tissue. Further anatomical measures that can be used to determine an increase in neuroprotection include counting specific neuronal cell types to determine if the progestin or the progestin metabolite is preferentially preserving a particular cell type (e.g., cholinergic cells) or neurons in general.

In addition, behavioral assays can be used to determine the rate and extent of behavior recovery in response to the treatment. Improved patient motor skills, spatial learning performance, cognitive function, sensory perception, speech and/or a decrease in the propensity to seizure may also be used to measure the neuroprotective effect. Such functional/behavioral tests used to assess sensorimortor and reflex function are described in, for example, Bederson et al. (1986) Stroke 17:472-476, DeRyck et al. (1992) Brain Res. 573:44-60, Markgraf et al. (1992) Brain Res. 575:238-246, Alexis et al. (1995) Stroke 26:2336-2346; all of which are herein incorporated by reference. Enhancement of neuronal survival may also be measured using the Scandinavian Stroke Scale (SSS) or the Barthl Index. Behavioral recovery can be further assessed using the recommendations of the Subcommittee of the NIH/NINDS Head Injury Centers in Humans (Hannay et al. (1996) J. Head Trauma Rehabil. 11:41-50), herein incorporated by reference. Behavioral recovery can be further assessed using the methods described in, for example, Beaumont et al. (1999) Neural Res. 21:742-754; Becker et al. (1980) Brain Res. 200:07-320; Buresov et al. (1983) Techniques and Basic Experiments for the Study of Brain and Behavior; Kline et al. (1994) Pharmacol. Biochem. Behav. 48:773-779; Lindner et al. (1998) J. Neurotrauma 15:199-216; Morris (1984) J. Neurosci. Methods 11:47-60; Schallert et al. (1983) Pharmacol. Biochem. Behav. 18:753-759.

Assays that can be used to determine if a compound is imparting an anti-inflammatory and a nonspecific suppressive effect on the immune system following a traumatic CNS injury include, for example, a reduction in cytokine induced microglial proliferation in vitro (Hoffman et al. (1994) J. Neurotrauma 11:417-31; Garcia-Estrada et al. (1993) Brain Res. 628:271-8; both of which are herein incorporated by reference); a reduction in the generation of cytotoxic free radicals by activated macrophages (Chao et al. (1994) Am. J. Reprod. Immunol. 32:43-52; Robert et al. (1997) Nitric Oxide 1:453-62; Kelly et al. (1997) Biochem. Biophys. Res. Commun. 239:557-61; Ganter et al. (1992) J. Neurosci. Res. 33:218-30; all of which are herein incorporated by reference); a reduction in the expression of inducible nitric oxide synthetase and the amount of nitric oxide release by macrophages (Robert et al. (1997) Nitric Oxide 1:453-62; Miller et al. (1996) J. Leukoc. Biol. 59:442-50; both of which are herein incorporated by reference); the release of a "progesterone-induced blocking factor" that inhibits natural killer cell activity (Cheek et al. (1997) Am. J. Reprod. Immunol. 37:17-20; Szekeres-Bartho et al. (1997) Cell Immunol. 177:194-9; Szekeres-Bartho et al. (1996) Am. J. Reprod. Immunol. 35:348-51; all of which are herein incorporated by reference); a decrease in the number of GF AP-positive astrocytes after brain injury which is suggestive of less secondary damage (Garcia-Estrada et al. (1993) Brain Res. 628:271-8; Garcie-Estrada et al. (1999) Int. J. Dev. Neurosci. 17:145-51; Cheek et al. (1997) Am. J. Reprod. Immunol. 37:17-20; Szekeres-Bartho et al. (1997) Cell Immunol. 177:194-9; Szekeres-Bartho et al. (1996) Am. J. Reprod. Immunol. 35:348-51; all of which are herein incorporated by reference); a reduction in the number of inflammatory immune cells (OX42-positive cells); a reduction in the loss of ChAT-positive and COX-positive neurons; a reduction in the number of TUNEL-positive and MnSOD-positive neurons; and an increase in the intensity of succinate dehydrogenase and cytochrome oxidase activity.

Furthermore, a reduction in the inflammatory immune reactions following a traumatic brain injury can be assayed by measuring the cytokines level following the injury in the sham controls versus the progestin treated subjects. Cytokines are mediators of inflammation and are released in high concentrations after brain injury. The level of pro-inflammatory cytokines (e.g., interleukin 1-beta, tumor necrosis factor, and interleukin 6) and the level of anti-inflammatory cytokines (e.g., interleukin 10 and transforming growth factor-beta) can be measured. For instance, "real-time" polymerase chain reactions (PCR) can be used to measure the strength of the mRNA signal and ELISA can be used to determine protein levels. In addition, histological analysis for different inflammatory cell types (e.g., reactive astrocytes, macrophages and microglia) can be used to measure a reduction in the inflammatory response.

The compounds disclosed herein can also have potential for use in other disorders including multiple sclerosis, catamenial epilepsy, diabetic neuropathy, inflammatory disorders (e.g., rheumatoid arthritis, inflammatory bowel disease), hemorrhagic shock, Niemann-Pick disorder, cerebral palsy, and congenital heart disorders.

In specific embodiments, the disclosure relates to a method of treatment or prevention of neural degeneration related to Amyotrophic Lateral Sclerosis (ALS) comprising administering a compound described herein, or a pharmaceutically acceptable salt, ester or prodrug thereof, to a patient suffering from or at risk of suffering from ALS. ALS, more commonly known as Lou Gehrig's Disease, strikes both males and females, typically between the ages of 40 and 70. This is a motor neuron disorder in which both the upper and lower motor neurons are affected. Patients' muscles atrophy as the motor neurons cease sending signals to initiate movement. This affects not only muscles required for locomotion but also the muscles used in swallowing. Life expectancy post-diagnosis is 2-5 years. The cause of ALS is uncertain, but excitotoxicity, inflammation, oxidative stress and protein aggregation have been shown. In some cases, super oxide dismutase I (SODI) has been determined to be aberrant. Glutamate toxicity is now generally accepted as part of AS pathology. Progesterone has proven to protect neurons from the effects of this toxicity. The only compound approved for the treatment of ALS is RILUTEK™ (i.e., riluzole) which may reduce glutamate levels. It is not curative but has reduced the rate of progression in some patients.

In another specific embodiment, the disclosure relates to a method of treatment or prevention of neural degeneration related to Parkinson's Disease (PD) comprising administering a compound described herein, or a pharmaceutically acceptable salt, ester or prodrug thereof, to a subject suffering from or at risk of suffering from PD. PD is a neurodegenerative disease of unknown etiology that results in the progressive loss of nerve cell function in the brain. In PD, cells in the substania nigra of the brain cease to function properly and die. These cells produce dopamine, a neurotransmitter. Dopamine regulates those parts of the brain which control the initiation of movement and coordination. Without dopamine, a patient will begin to experience tremors, bradykinesia, postural instability, rigidity of limbs and trunk, and/or impaired balance and coordination. Not all patients experience all symptoms nor do they progress at the same rate.

In another embodiment, the disclosure relates to a method of treating or preventing neural degeneration related to spinal cord trauma comprising administering a compound described herein, or a pharmaceutically acceptable salt, ester or prodrug thereof, to a patient in need thereof. In another specific embodiment, a method of treatment or prevention of neural degeneration related to hypoxia is provided comprising administering a steroid analog described herein, or a pharmaceutically acceptable salt, ester or prodrug thereof, to a patient in need thereof.

Hormone Therapies

Within certain embodiments, the disclosure relates to using compounds disclosed herein for any therapies that progesterone is typically utilized such as hormonal therapies. In certain embodiments, compounds disclosed herein may be used to support pregnancy in Assisted Reproductive Technology (ART) cycles such as In-vitro Fertilization (IVF). In vitro fertilization (IVF) is the technique of letting fertilization of the male and female gametes (sperm and egg) occur outside the female body. Techniques usually used in in vitro fertilization include transvaginal ovum retrieval and embryo transfer. Transvaginal ovum retrieval is a process whereby a needle is inserted through the back of the vagina and guided via ultrasound into the ovarian follicles to collect the fluid that contains the eggs. Embryo transfer is the step in the process whereby one or several embryos are placed into the uterus of the female with the intent to establish a pregnancy. Compounds disclosed herein, optionally in combination with progesterone, may be administered to the uterus to improve the likelihood of pregnancy.

In certain embodiments, the disclosure relates to administering compounds disclosed herein to a subject in order to control persistent anovulatory bleeding, prepare uterine lining in infertility therapy, and to support early pregnancy. Patients with recurrent pregnancy loss due to inadequate progesterone production may receive compounds disclosed herein optionally in combination with progesterone.

In certain embodiments, the discloser relates to administering compounds disclosed herein for preventing preterm birth in women at risk for preterm birth. In certain embodiments, the subject is a women with a short cervix. In certain embodiments, the compounds are administered after pregnancy or 3, 4, 5, 6, 7, or 8 months after conception up until birth.

In certain embodiments, the disclosure relates to methods of treating or preventing endometrial hyperplasia comprising administering an effective amount of a compound or a pharmaceutical composition comprising a compound disclosed herein to a subject in need thereof. In certain embodiments, the subject is a non-hysterectomized postmenopausal women. In certain embodiments, the pharmaceutical composition is administered in combination with estrogen.

In certain embodiments, the disclosure relates to methods of treating or preventing secondary amenorrhoea comprising administering a compound or a pharmaceutical composition comprising a compound disclosed herein to a subject in need thereof.

In certain embodiments, the disclosure relates to methods of providing immunosuppression comprising administering an effective amount of a compound or a compound or a pharmaceutical composition comprising a compound disclosed herein to a subject in need thereof. In certain embodiments, the subject is the recipient of an organ transplant. In certain embodiments, the pharmaceutical composition is administered in combination with a second immunosuppressive agent.

EXPERIMENTAL

Example 1

Synthesis of Compounds (E)-(((1-(10,13-dimethyl-3-oxo-2,3,6,7,8,9,10,11,12,13,14,15,16,17-tetradecahydro-1H-cyclopenta[a]phenanthren-17-yl)ethylidene)amino)oxy)methyl dihydrogen phosphate [EPRX-01723]

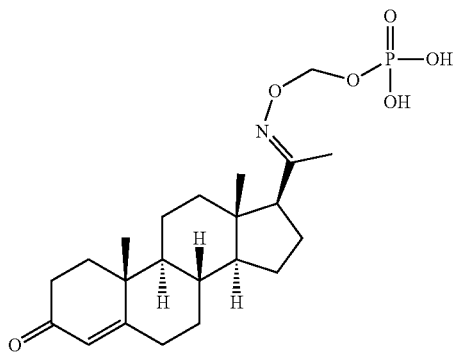

Figure 3:
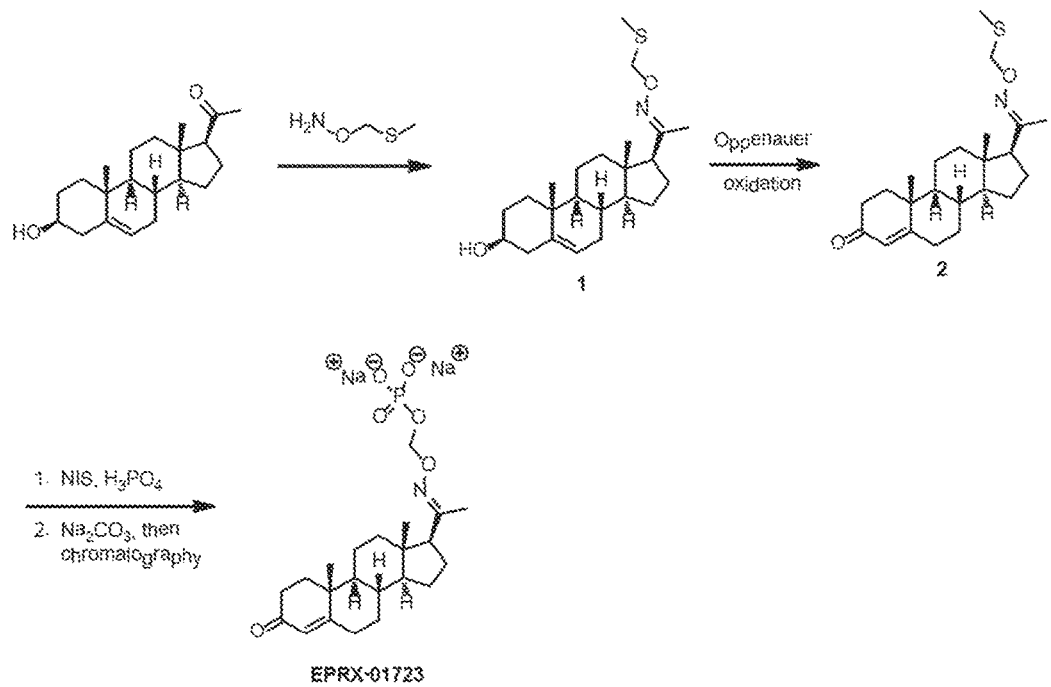
FIG. 3 illustrates the preparation of certain embodiments of the disclosure.

The preparation of this compound is illustrated in FIG. 3. 3β-Hydroxypregn-5-en-20-one is condensed with O-((methylthio)methyl)hydroxylamine to give the oxime compound as a single oxime isomer (E). Standard Oppenauer oxidation conditions produce the ketone oxime compound. Displacement of the methylthio group with the phosphate group is accomplished with phosphoric acid in the presence of N-iodosuccinimide, followed by conversion to the disodium salt and purification by reverse-phase column chromatography, gives EPRX-01723.

(((E)-(17-acetyl-10,13-dimethyl-7,8,9,11,12,13,14,15,16,17-decahydro-1H-cyclopenta[a]phenanthren-3(2H,6H,10H)-ylidene)amino)oxy)methyl dihydrogen phosphate [EPRX-01619]

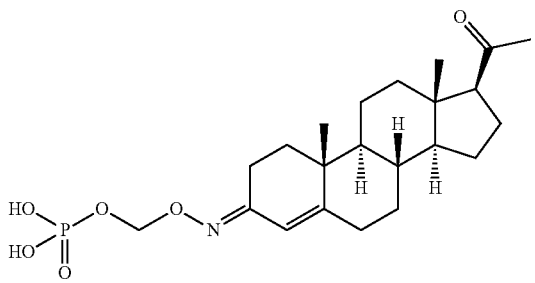

Figure 4:
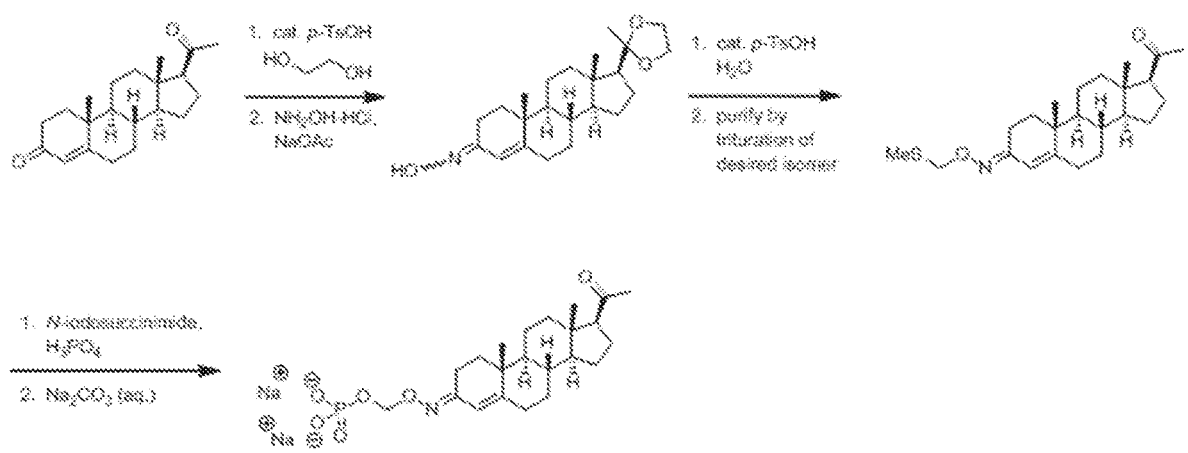
FIG. 4 illustrates the preparation of certain embodiments of the disclosure.
Figure 5:
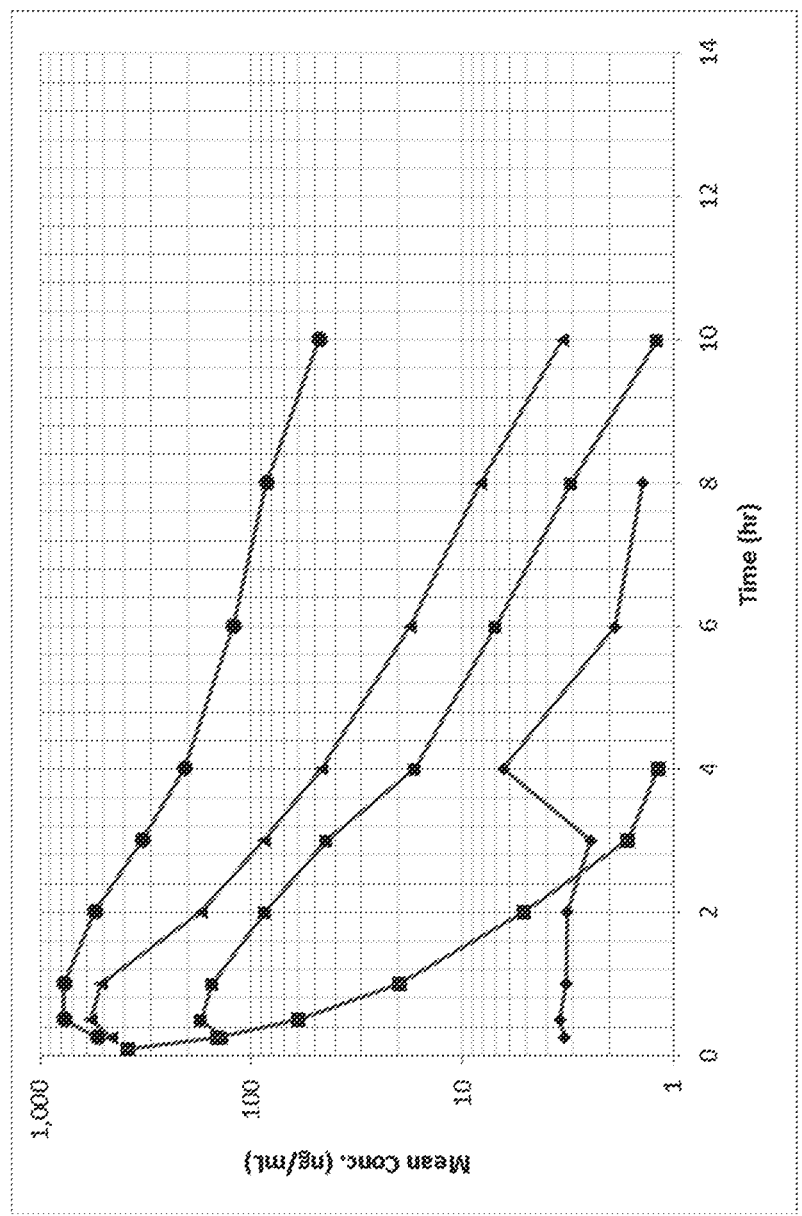
FIG. 5 shows data of IV, IM, and PO dosing of EPRX01723 in rat plasma. The pharmacokinetics of EPRX-1723 (POM derivative of C-20 oxime) was determined after IM dosing at 3 different levels and showed exposure of the relative C-20 oxime parent (EPRX-036) indicating that the solubilizing prodrug is efficiently cleaved in vivo to give the active parent oxime. Diamond represents PO (30 mg/kg), orange box represents IM (3 mg/kg), green triangle represents IM (10 mg/kg), yellow box represents IM (30 mg/kg), brown box represents IV (2 mg/kg), red circle represents IM (0 mg/kg).

The preparation of this compound is illustrated in FIG. 4. Selective protection of progesterone at the C-20 ketone is accomplished in ethylene glycol in the presence of an acid catalyst. Condensation with O-((methylthio)methyl)hydroxylamine gives two geometric oxime isomers which are separated from each other to provide the E configuration. Ketal deprotection is accomplished with an acid catalyst. Displacement of the methylthio group with the phosphate group is accomplished with phosphoric acid in the presence of N-iodosuccinimide, followed by conversion to the disodium salt and purification by reverse-phase column chromatography, gives EPRX-01619.

1-((8S,9S,10R,13S,14S,17S,E)-3-(Hydroxyimino)-10,13-dimethyl-2,3,6,7,8,9,10,11,12,13,14,15,16,17-tetradecahydro-1H-cyclopenta[a]phenanthren-17-yl)ethanone (2).

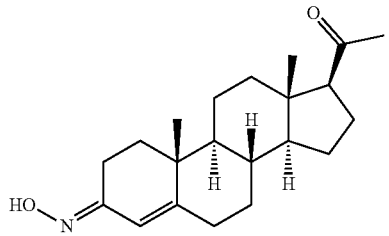

A round bottom flask was charged with solid (8S,9S,10R,13S,14S,17S,E)-10,13-dimethyl-17-(2-methyl-1,3-dioxolan-2-yl)-6,7,8,9,10,11,12,13,14,15,16,17-dodecahydro-1H-cyclopenta[a]phenanthren-3(2H)-one oxime (1.00 g, 2.68 mmol) and dissolved in acetone (150 mL) at ambient temperature under nitrogen. See MacNevin et al., J. Med. Chem., 2009, 52 (19), 6012-6023, hereby incorporated by reference. p-Toluenesulfonic acid monohydrate (0.102 g, 0.54 mmol) was added, and the mixture was stirred at ambient temperature 2.5 h. The mixture was concentrated by rotary evaporation, and the residue was purifed by flash chromatography (0-20% EtOAc in hexanes) to afford 2 (0.30 g, 34% yield) as a white solid.

tert-Butyl (S)-1-((E)-((8S,9S,10R,13S,14S,17S)-17-acetyl-10,13-dimethyl-7,8,9,11-tetrahydro-1H-cyclopenta[a]phenanthren-3(2H,6H,10H,12H,13H,14H,15H,16H,17H)-ylidene)aminooxy)-3-methyl-1-oxobutan-2-ylcarbamate (S1).

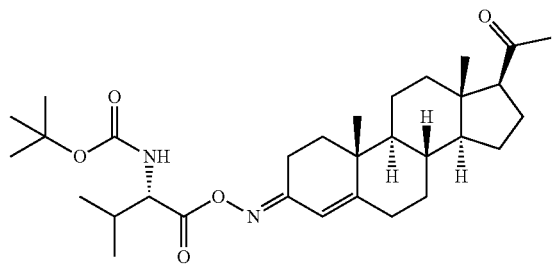

A round bottom flask was charged with solid 2 (2.6 g, 7.89 mmol) and dichloromethane (30 mL) under nitrogen with stirring. Solid L-Boc-Val-OH (3.43 g, 15.8 mmol) was added all at once to the solution, followed by DMAP (0.096 g, 0.79 mmol), and DIPEA (2.75 mL, 15.8 mmol) was added dropwise via syringe. EDCI (3.03 g, 15.8 mmol) was added in one portion, the reaction mixture was allowed to slowly come to room temperature, and was stirred at ambient temperature for 18 h. Saturated aqueous sodium bicarbonate (50 mL) was added, the organic layer was removed, and the aqueous layer was extracted with dichloromethane (3×50 mL). The combined organic layers were washed sequentially with water (3×50 mL) and brine (3×50 mL), dried over sodium sulfate, filtered, and concentrated under reduced pressure. The yellow oil was purified by flash chromatography (10-30% EtOAc in hexanes) to afford S1 (3.80 g, 91%) as a white solid.

(S)-1-((E)-((8S,9S,10R,13S,14S,17S)-17-Acetyl-10,13-dimethyl-7,8,9,11-tetrahydro-1H-cyclopenta[a]phenanthren-3(2H,6H,10H,12H,13H,14H,15H,16H,17H)-ylidene)aminooxy)-2-amino-3-methylbutan-1-one hydrochloride (1).

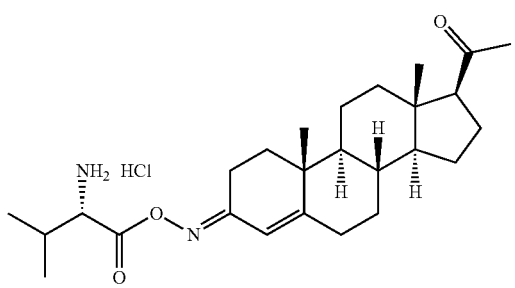

A round bottom flask was charged with solid S1 (2.20 g, 4.16 mmol), 13 mL of dichloromethane was added, and the stirred solution was cooled to 0° C. under nitrogen using an ice bath. TFA (13 mL, 169 mmol) was slowly added over a 15 minute period, and stirring was continued at 0° C. until reaction was complete, about 1 h. The mixture was concentrated under reduced pressure at <20° C. and the resulting light pink oil was dried in vacuo for 1 h. Dioxane (3 mL) was added to the residue and cooled to 0° C. using an ice bath; 4.0 M HCl-dioxane solution was added dropwise (1.56 mL, 6.24 mmol) and stirring was continued at 0° C. for an additional 30 minutes. Ether (50 mL) was added, the mixture was stirred at 0° C. for 15 minutes, and the supernatant was decanted from the white solid. The solid was triturated with additional ether (3×50 mL) and dried in vacuo to afford 1 (1.50 g, 78% yield) as a white solid, mp 159-161° C.

(E)-1-((3S,8S,9S,10R,13S,14S,17S)-3-Hydroxy-10,13-dimethyl-2,3,4,7,8,9,10,11,12,13,14,15,16,17-tetradecahydro-1H-cyclopenta[a]phenanthren-17-yl)ethanone oxime (S2). See. Vasil'tov et al., Chemistry of Heterocyclic Compounds, 2001, 37(12), 1488-1492 and Kim et al., Molecules, 2009, 14, 4655-4668.

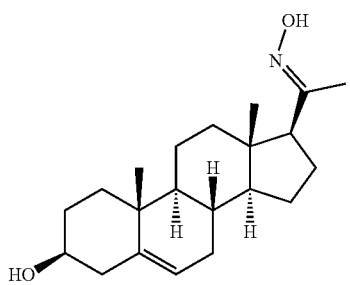

A round bottom flask was charged with 5-pregnen-3β-ol-20-one (20.6 g, 65.1 mmol) and methanol (500 mL), and the mixture was heated to reflux with stirring to dissolve all solids. Hydroxylamine hydrochloride (9.05 g, 130 mmol) and sodium acetate (11.75 g, 143 mmol) were dissolved in water (30 mL), and this solution was added to the solution over 3 h. After addition was complete, the mixture was refluxed for an additional 3 h; a white precipitate formed during this time. The mixture was cooled to ambient temperature, water (300 mL) was added, and the resulting mixture was stirred for 45 minutes. The solids were collected by vacuum filtration, washed with additional water (3×300 mL), and dried in vacuo to afford S2 (21.0 g, 97% yield) as a white solid, mp 210° C. (dec.). Spectral data agreed with that previously reported in the literature:
$^1$H NMR (400 MHz, CDCl$_3$) δ: 8.05 (br s, 1H), 5.41-5.31 (m, 1H), 3.54 (well defined multiplet centered at 3.54, 1H), 2.34-2.19 (m, 2H), 2.14-1.98 (m, 2H), 1.94-1.82 (m, 1H), 1.90 (s, 3H), 1.75-1.42 (m, 10H), 1.35-0.95 (m, 6H), 1.02 (s, 3H), 0.65 (s, 3H).

(8S,9S,10R,13S,14S,17S)-17-((E)-1-(Hydroxyimino)ethyl)-10,13-dimethyl-6,7,8,9,10,11,12,13,14,15,16,17-dodecahydro-1H-cyclopenta[a]phenanthren-3 (2H)-one (3).

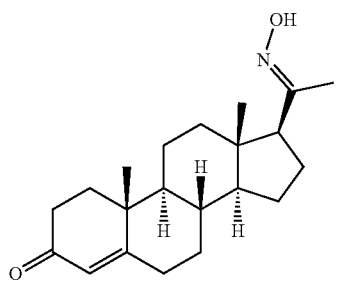

A round bottom flask fitted with a reflux condenser and Dean-Stark trap was charged with solid S2 (21.0 g, 63.3 mmol), N-methylpiperidone (73.1 ml, 633 mmol), and toluene (500 mL). The resulting mixture was heated to reflux for 2 h for azeotropic removal of adventitious water. Aluminum isopropoxide (25.9 g, 127 mmol) was slowly added to the clear solution, and the resulting mixture was refluxed for 18 h. The dark orange mixture was cooled to ambient temperature, and a saturated aqueous Rochelle salt solution (300 mL) was slowly added over 30 min with stirring. After further stirring for 45 min, the layers were separated, and the aqueous layer was extracted with dichloromethane (3×200 mL). The combined organic layers were washed with water (3×150 mL) and brine (1×100 mL), dried over sodium sulfate, filtered, and concentrated by rotary evaporation. The dark orange oil was taken up in 50% EtOAc/DCM and passed through a plug of silica gel, eluting with 1 L of 50% EtOAc/DCM. The filtrate was concentrated under reduced pressure and purified by silica gel chromatography (5-20% EtOAc in DCM) to afford 3 (16.0 g, 77% yield) as a white solid.

(E)-1-((3S,8S,9S,10R,13S,14S,17S)-3-Hydroxy-10,13-dimethyl-2,3,4,7,8,9,10,11,12,13,14,15,16,17-tetradecahydro-1H-cyclopenta[a]phenanthren-17-yl)ethanone O-methyl oxime (S3).

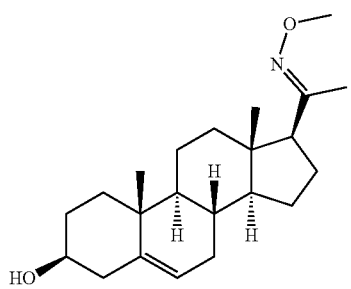

A round bottom flask fitted with a reflux condenser was charged with 5-pregnen-3β-ol-20-one (3.16 g, 10.0 mmol), methoxylamine hydrochloride (0.92 g, 11.0 mmol) and pyridine (10 mL). The mixture was heated to 95° C. for 3 h, cooled to room temperature, and poured into water (100 mL). The white solid was collected by vacuum filtration, washed with water (3×100 mL), and dried in vacuo. The crude solid was purified by flash chromatography (85:15 CH$_2$Cl$_2$:EtOAc) to afford S3 (2.75 g, 87% yield) as a white solid.

(8S,9S,10R,13S,14S,17S)-17-((E)-1-(Methoxyimino)ethyl)-10,13-dimethyl-6,7,8,9,10,11,12,13,14,15,16,17-dodecahydro-1H-cyclopenta[a]phenanthren-3(2H)-one (4).

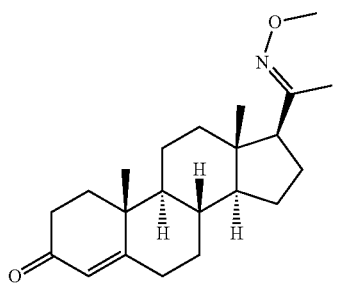

A round bottom flask fitted with a Dean-Stark trap and a reflux condenser was charged with S3 (1.73 g, 5.00 mmol), N-methyl-4-piperidone (5.66 g, 50 mmol) and toluene (50 mL). The mixture was refluxed for 1 h for azeotropic removal of adventitious water, was cooled to ambient temperature, and aluminum isopropoxide (2.04 g, 10 mmol) was added in one portion. The mixture was refluxed for 18 h, cooled to ambient temperature, and treated by stirring with saturated aqueous Rochelle salt solution (25 mL) for 2 h. The layers were separated, and the aqueous layer was extracted with DCM (3×25 mL). The combined organic layers were washed with water (3×50 mL) and brine (3×50 mL), dried over Na$_2$SO$_4$, filtered, and concentrated by rotary evaporation. The crude orange solid was purified by flash chromatography (3:1 hexanes:EtOAc) to afford 4 (1.06 g, 62% yield) as a white solid.

(E)-1-((3S,8S,9S,10R,13S,14S,17S)-3-Hydroxy-10,13-dimethyl-2,3,4,7,8,9,10,11,12,13,14,15,16,17-tetradecahydro-1H-cyclopenta[a]phenanthren-17-yl)ethanone O-2-morpholinoethyl oxime (S4): See Courtney et al., WO 2008142720 and Chen et al., WO 2009097578.

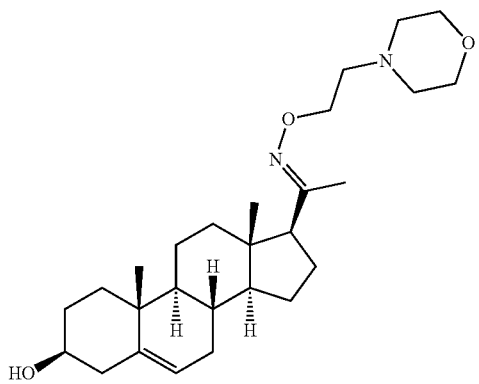

A round bottom flask was charged with O-(2-morpholinoethyl)hydroxylamine dihydrochloride (1.97 g, 9.0 mmol), sodium acetate (1.60 g, 19.5 mmol), and 5-pregnen-3β-ol-20-one (2.37 g, 7.5 mmol). The flask was fitted with a reflux condenser, and MeOH (40 mL) was added along with water (4 mL). The mixture was refluxed with stirring for 16 h. The reaction mixture was cooled to ambient temperature and was partitioned between saturated aqueous NaHCO$_3$ (100 mL) and dichloromethane (150 mL). The aqueous layer was extracted with additional DCM (2×150 mL), and the combined organic layers were dried over Na$_2$SO$_4$, filtered, and concentrated by rotary evaporation. The crude solid was purified by flash chromatography using a CombiFlash (80 g column, 2 to 10% EtOH in EtOAc) to afford S4 (2.79 g, 84% yield) as a white, flaky solid.

(8S,9S,10R,13S,14S,17S)-10,13-Dimethyl-17-((E)-1-(2-morpholinoethoxyimino)ethyl)-6,7,8,9,10,11,12,13,14,15,16,17-dodecahydro-1H-cyclopenta[a]phenanthren-3(2H)-one (5).

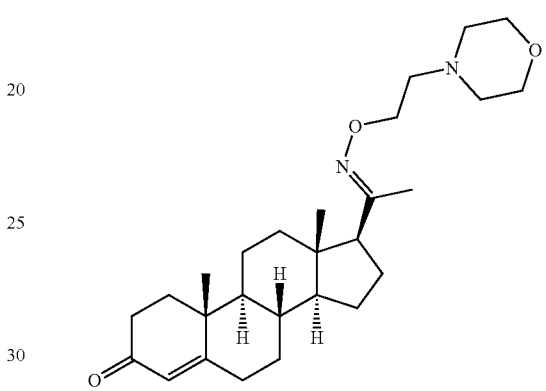

A round bottom flask fitted with a reflux condenser and Dean-Stark trap was charged with S4 (1.56 g, 3.50 mmol), N-methyl-4-piperidone (3.96 g, 35 mmol), and toluene (30 mL). The mixture was refluxed for 1 h for azeotropic removal of adventitious water, and recooled to room temperature. Aluminum isopropoxide (1.43 g, 7.0 mmol) was added all at once, and the mixture was returned to reflux with stirring. After refluxing 20 h, the mixture was cooled to ambient temperature and was treated with saturated aqueous Rochelle salt solution (50 mL) by stirring for 2 h. The mixture was extracted with DCM (3×100 mL). The combined organic layers were dried over Na$_2$SO$_4$, filtered, and concentrated by rotary evaporation. The crude orange oil was purified by flash chromatography using a CombiFlash (80 g column, 1 to 10% EtOH in EtOAc) to afford 5 (1.21 g, 78% yield) as a white solid.

(8S,9S,10R,13S,14S,17S)-17-((E)-1-(acetoxyimino)ethyl)-10,13-dimethyl-6,7,8,9,10,11,12,13,14,15,16,17-dodecahydro-1H-cyclopenta[a]phenanthren-3(2H)-one (6).

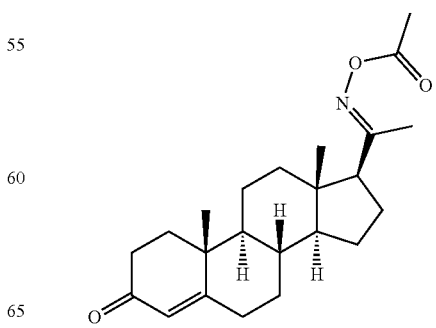

A round bottom flask was charged with 3 (0.82 g, 2.5 mmol) and pyridine (5 mL) under nitrogen with stirring at room temperature. Acetic anhydride (1.7 mL, 18.0 mmol) was added all at once via syringe, followed by DMAP (0.050 g, 0.40 mmol). The mixture was stirred for 18 h at ambient temperature, then diluted with dichloromethane (50 mL), washed with saturated aqueous NH$_4$Cl (3×50 mL) and brine (1×50 mL), dried over Na$_2$SO$_4$, filtered, and concentrated by rotary evaporation. The residue was purified by flash chromatography using a Combiflash (25 g column, 1 to 10% EtOAc in DCM) to afford 6 (0.71 g, 76% yield) as a white solid.

tert-Butyl (S)-1-((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylideneaminooxy)-3-methyl-1-oxobutan-2-ylcarbamate (S5).

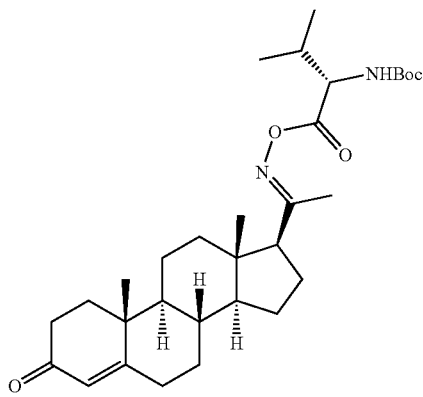

A round bottom flask was charged with 3 (3.29 g, 10.0 mmol), L-Boc-Val-OH (4.34 g, 20.0 mmol), DMAP (0.122 g, 1.00 mmol), and dichloromethane (50 mL) under nitrogen at 0° C. To the stirred solution was added N,N-diisopropylethylamine (3.48 mL, 20.0 mmol) all at once via syringe, followed by EDCI (3.83 g, 20.0 mmol) in one portion, and the resulting mixture was stirred for 18 h at ambient temperature. Saturated aqueous NH$_4$Cl (100 mL) was added, the organic layer was removed, and the aqueous layer was extracted with dichloromethane (3×50 mL). The combined organic layers were washed with brine (1×50 mL), dried over Na$_2$SO$_4$, filtered, and concentrated by rotary evaporation. Purification by flash chromatography (3:2 hexanes:EtOAc) afforded S5 (4.87 g, 92%) as a white solid.

(8S,9S,10R,13S,14S,17S)-17-((E)-1-((S)-2-Amino-3-methylbutanoyloxyimino)ethyl)-10,13-dimethyl-6,7,8,9,10,11,12,13,14,15,16,17-dodecahydro-1H-cyclopenta[a]phenanthren-3(2H)-one hydrochloride (7).

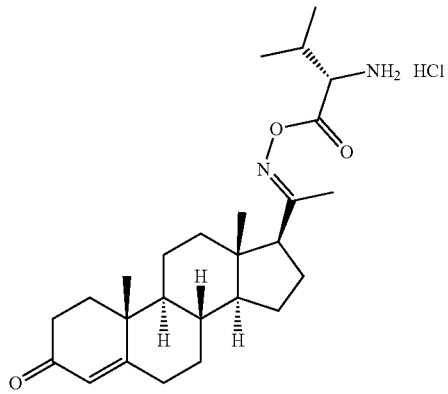

Solid S5 (1.06 g, 2.0 mmol) was dissolved in dichloromethane (6 mL) at 0° C. under nitrogen with stirring. TFA (6 mL) was added dropwise via syringe with stirring, and the mixture was stirred at 0° C. for 90 min. The volatiles were removed by rotary evaporation, and the residue was dried in vacuo for 2 h. The resulting brown oil was cooled to 0° C. with stirring under nitrogen, and a solution of 4.0 M HCl in dioxane (0.60 mL, 2.4 mmol) was added dropwise via syringe. The mixture was stirred 5 minutes, then Et$_2$O (20 mL) was added. The resulting mixture was warmed to ambient temperature, stirred for 20 minutes, and collected by vacuum filtration. The solids were washed with additional Et$_2$O (2×20 mL) and dried in vacuo to afford 7 (0.91 g, 95% yield) as a white solid.

(S)-tert-Butyl 2-(((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylideneaminooxy)carbonyl)pyrrolidine-1-carboxylate (S6).

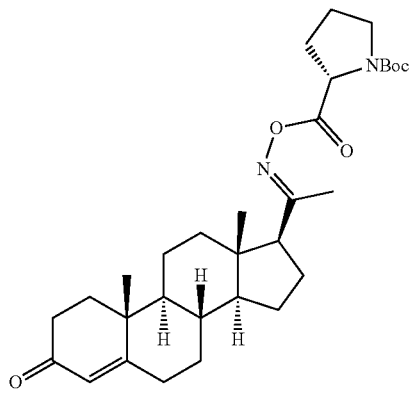

A round bottom flask was charged with 3 (0.659 g, 2.00 mmol), L-Boc-Pro-OH (0.861 g, 4.00 mmol), DMAP (0.024 g, 0.20 mmol), and dichloromethane (20 mL) under nitrogen at 0° C. To the stirred solution was added N,N-diisopropylethylamine (0.697 mL, 4.00 mmol) all at once via syringe, followed by EDCI (0.767 g, 4.00 mmol) in one portion, and the resulting mixture was stirred for 18 h at ambient temperature. Saturated aqueous NH$_4$Cl (20 mL) was added, the organic layer was removed, and the aqueous layer was extracted with dichloromethane (3×20 mL). The combined organic layers were washed with brine (1×40 mL), dried over Na₂SO₄, filtered, and concentrated by rotary evaporation. Purification using the Combiflash (40 g column, 10 to 50% EtOAc in hexanes) afforded S6 (0.974 g, 92%) as a white solid.

(8S,9S,10R,13S,14S,17S)-10,13-Dimethyl-17-((E)-1-((S)-pyrrolidine-2-carbonyloxyimino)ethyl)-6,7,8,9,10,11,12,13,14,15,16,17-dodecahydro-1H-cyclopenta[a]phenanthren-3(2H)-one hydrochloride (8).

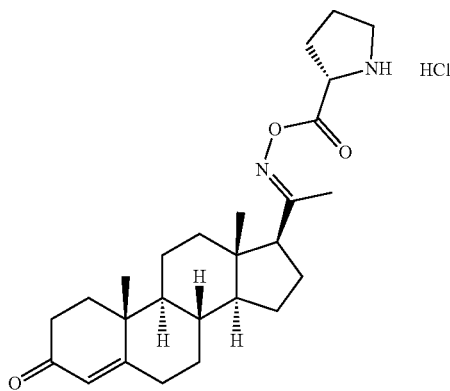

A round bottom flask was charged with S6 (0.53 g, 1.00 mmol) and dichloromethane (3 mL), and the stirred solution was cooled to 0° C. under nitrogen. Trifluoroacetic acid (4.56 g, 40 mmol) was slowly added via syringe, and the solution was stirred 2 h at 0° C. Volatiles were removed by rotary evaporation (bath temperature<10° C.) and dried further in vacuo. The residue was treated with a 4.0 M dioxane solution of HCl in dioxane (1.2 mmol, 0.30 mL) at 0° C. and stirred for 15 min. Ether (25 mL) was added, and stirring continued for an additional 15 min at ambient temperature. The supernatant was decanted, and the solid was triturated with ether (3×25 mL). The solid was dried in vacuo to afford 8 (0.40 g, 87% yield) as a white solid (8S,9S,10R,13S,14S,17S)-10,13-Dimethyl-17-((E)-1-((S)-1,1-Dimethylpyrrolidine-2-carbonyloxyimino)ethyl)-6,7,8,9,10,11,12,13,14,15,16,17-dodecahydro-1H-cyclopenta[a]phenanthren-3(2H)-one iodide (9). See Han et al., Eur. J. Org. Chem., 2005, 5, 934-938.

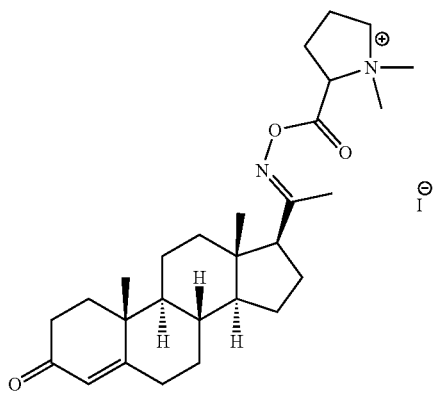

A round bottom flask was charged with solid 3 (0.99 g, 3.0 mmol), N-methyl-L-proline5 (0.78 g, 6.0 mmol), (0.04 g, 0.30 mmol), and dichloromethane (30 mL) under nitrogen. The stirred mixture was cooled to 0° C., and N,N-diisopropylethylamine (1.05 mL, 6.0 mmol) was added via syringe. Solid EDCI (1.15 g, 6.0 mmol) was added in one portion, and the mixture was stirred at ambient temperature for 18 h. Saturated aqueous NaHCO₃ (30 mL) was added, and the organic layer was removed. The aqueous layer was extracted with dichloromethane (3×30 mL) and the combined organic layers were washed with brine (1×30 mL), dried over Na₂SO₄, filtered, and concentrated by rotary evaporation. The residue was purified by flash chromatography using a Combiflash (40 g column, 0 to 100% EtOAc in DCM) to afford 1.1 g of desired coupling product in ~90% purity as determined by 1H NMR. A second attempt at purification by additional chromatography resulted in further degradation (0.56 g crude, ~80% pure), and the material was used as-is for the next step.

A round bottom flask was charged with the 0.56 g of crude material from the previous step, methyl iodide (0.63 mL, 10.1 mmol), and acetone (20 mL). The mixture was refluxed under nitrogen for 2 h, during which time a white solid precipitated. After cooling to ambient temperature, the solid was collected by vacuum filtration, washed with additional acetone (2×20 mL), and dried in vacuo to afford 9 (0.45 g, 25% over 2 steps) as a white solid (8S,9S,10R,13S,14S,17S)-17-((E)-1-(2-(Dimethylamino)acetoxyimino)ethyl)-10,13-dimethyl-6,7,8,9,10,11,12,13,14,15,16,17-dodecahydro-1H-cyclopenta[a]phenanthren-3(2H)-one (10).

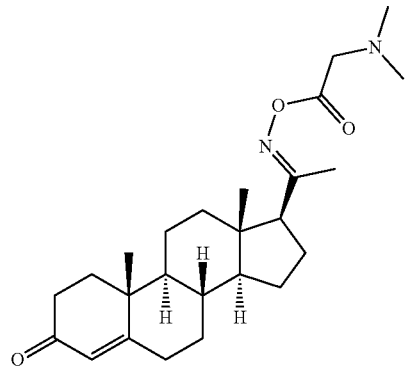

A round bottom flask was charged with 3 (0.66 g, 2.0 mmol) and dichloromethane (20 mL), and the stirred solution was cooled to 0° C. under nitrogen. N,N-Dimethylglycine (0.52 g, 5.0 mmol), DMAP (0.073 g, 0.60 mmol), and N,N-diisopropylethylamine (0.87 mL, 5.0 mmol) were added to the solution. EDCI (0.96 g, 5.0 mmol) was added in one portion, the mixture was warmed to ambient temperature, and was stirred for 18 h. Saturated aqueous NaHCO₃ (20 mL) was added, the layers were separated, and the aqueous layer was extracted with dichloromethane (2×20 mL). The combined organic layers were washed with brine (1×40 mL), dried over Na₂SO₄, filtered, and concentrated by rotary evaporation. The crude yellow oil was purified by flash chromatography using a Combiflash (40 g column, 0 to 10% EtOH in EtOAc) to yield 10 (0.62 g, 73% yield) as a white solid.

(8S,9S,10R,13S,14S,17S)-17-((E)-1-(2-(triimethylamino)acetoxyimino)ethyl)-10,13-dimethyl-6,7,8,9,10,11,12,13,14,15,16,17-dodecahydro-1H-cyclopenta[a]phenanthren-3(2H)-one iodide (11).

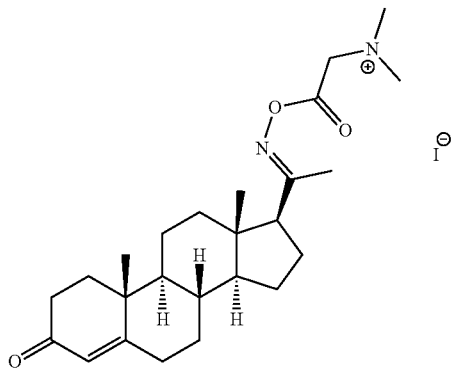

A round bottom flask was charged with 10 (0.10 g, 0.25 mmol) and acetone (5 mL) under nitrogen with stirring. Iodomethane (0.16 mL, 2.50 mmol) was added, and the mixture was refluxed for 4 h; the solution turned yellow and a precipitate formed after 5 min. The mixture was cooled to ambient temperature and the supernatant was decanted. The solid was triturated with acetone (2×10 mL) at ~70° C. and dried in vacuo to yield 11 (0.74 g, 53% yield) as a yellow solid.

(8S,9S,10R,13S,14S,17S)-10,13-Dimethyl-17-((E)-1-(2-morpholinoacetoxyimino)ethyl)-6,7,8,9,10,11,12,13,14,15,16,17-dodecahydro-1H-cyclopenta[a]phenanthren-3(2H)-one (12). See Fedi et al., J. Med. Chem. 2004, 47, 6935-6947.

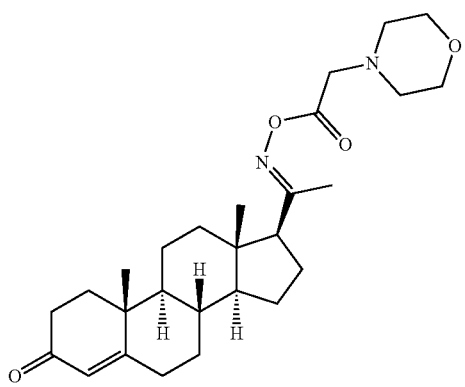

A round bottom flask was charged with 3 (0.659 g, 2.00 mmol), DMAP (0.073 g, 0.60 mmol), 2-morpholinoacetic acid (1.30 g, 5.00 mmol) and dichloromethane (20 mL) with stirring under nitrogen at 0° C. N,N-Diisopropylethylamine (1.74 mL, 10.00 mmol) was added via syringe, followed by addition of EDCI (0.959 g, 5.00 mmol) in a single portion. The resulting solution was stirred at ambient temperature for 18 h. The mixture was poured into saturated aqueous NaHCO$_3$ (20 mL) and the organic layer was removed. The aqueous layer was extracted with dichloromethane (2×20 mL), and the combined organic layers were washed with brine (1×40 mL), dried over Na$_2$SO$_4$, filtered, and concentrated by rotary evaporation. The crude was purified using a Combiflash (80 g column, 0.5 to 10% EtOH in EtOAc) to yield 12 (0.861 g, 94% yield) as an off-white solid.

(8S,9S,10R,13S,14S,17S)-10,13-Dimethyl-17-((E)-1-(2-(4-methylpiperazin-1-yl)acetoxyimino)ethyl)-6,7,8,9,10,11,12,13,14,15,16,17-dodecahydro-1H-cyclopenta[a]phenanthren-3(2H)-one (13).

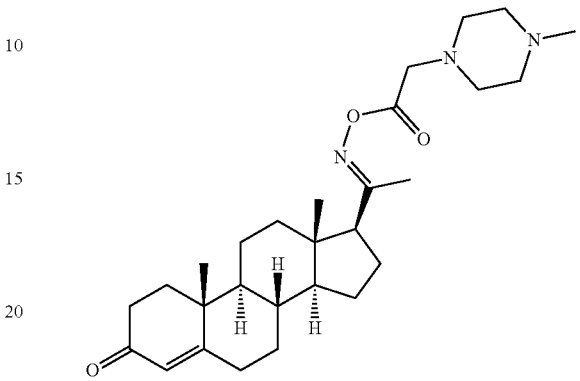

A round bottom flask was charged with 3 (0.33 g, 1.0 mmol), 2-(4-methylpiperazin-1-yl)acetic acid (0.32 g, 2.0 mmol), and dichloromethane (10 mL) under nitrogen with stirring. The solution was cooled to 0° C., and DMAP (0.012 g, 0.10 mmol) and N,N-diisopropylethylamine (0.35 mL, 2.0 mmol) were added, followed by addition of EDCI (0.38 g, 2.0 mmol) in one portion. After stirring for 16 h at ambient temperature, the mixture was poured into saturated aqueous NaHCO$_3$ (10 mL) and the organic layer was removed. The aqueous layer was extracted with DCM (3×20 mL), and the combined organics were washed with brine (1×40 mL), dried over Na$_2$SO$_4$, filtered, and concentrated by rotary evaporation. The crude yellow oil was purified using a Combiflash (40 g column, 0.5 to 10% MeOH in DCM) to afford 13 (0.46 g, 98% yield) as a pale yellow oil that solidified upon standing.

(8S,9S,10R,13S,14S,17S)-10,13-Dimethyl-17-((E)-1-(picolinoyloxyimino)ethyl)-6,7,8,9,10,11,12,13,14,15,16,17-dodecahydro-1H-cyclopenta[a]phenanthren-3(2H)-one (14).

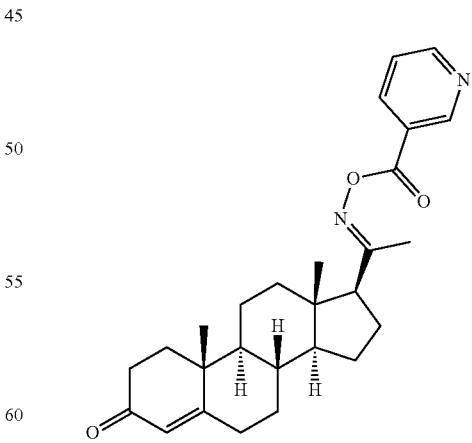

A round bottom flask was charged with 3 (0.66 g, 2.00 mmol), nicotinic acid (0.74 g, 6.00 mmol), and dichloromethane (20 mL) with stirring under nitrogen. The solution was cooled to 0° C., and DMAP (0.073 g, 0.60 mmol) and N,N-diisopropylethylamine (0.78 g, 6.00 mmol) were added, followed by EDCI (1.15 g, 6.00 mmol). After stirring for 16 h at ambient temperature, the reaction was quenched by the addition of water (20 mL) and the organic layer was removed. The aqueous layer was extracted with dichloromethane (3×20 mL). The combined organic layers were washed with water (3×20 mL) and brine (1×20 mL), dried over $Na_2SO_4$, filtered, and concentrated by rotary evaporation. The dark orange oil was purified using a Combiflash (40 g column, 0 to 30% EtOAc in DCM) to afford 14 (0.70 g, 80% yield) as a white solid.

3-(((E)-1-((8S,9S,10R,13S,14S,17S)-10,13-Dimethyl-3-oxo-2,3,6,7,8,9,10,11,12,13,14,15,16,17-tetradecahydro-1H-cyclopenta[a]phenanthren-17-yl)ethylideneaminooxy)carbonyl)-1-methylpyridinium iodide (15).

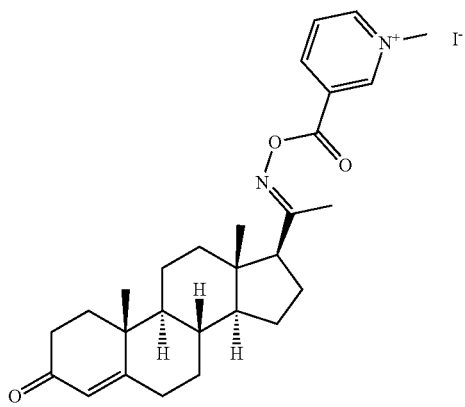

A round bottom flask was charged with 14 (0.54 g, 1.25 mmol), acetone (25 mL), and iodomethane (0.78 mL, 12.5 mmol) under nitrogen. The mixture was refluxed for 5 h; the solution turned yellow and precipitate formed after 5 minutes. The mixture was cooled to ambient temperature and the supernatant was decanted. The solid was triturated with acetone (3×50 mL) and dried in vacuo to yield 15 (0.52 g, 65% yield) as a bright yellow solid tert-Butyl 4-(((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylideneaminooxy)carbonyl)benzylcarbamate (S7). See Erdelyi et al., Organic & Biomolecular Chemistry, 2008, 6(23), 4356-4373.

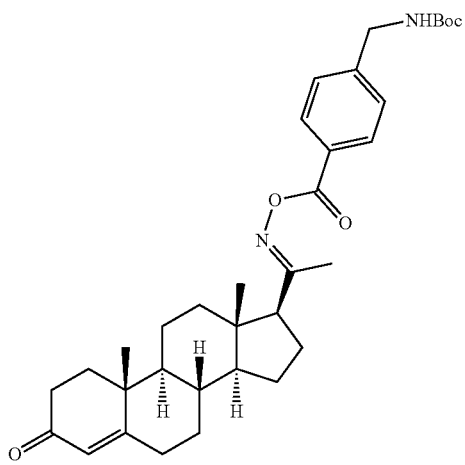

A round bottom flask was charged with 3 (1.65 g, 5.0 mmol), 4-(Boc-aminomethyl)benzoic acid (2.51 g, 10.0 mmol), and DMAP (0.122 g, 1.000 mmol) in dichloromethane (50 mL) under nitrogen. The stirred solution was cooled to 0° C. N,N-Diisopropylethylamine (1.74 mL, 10.0 mmol) was added, followed by solid EDCI (1.92 g, 10.0 mmol) in one portion. The mixture was slowly warmed to ambient temperature and stirred 18 h. The mixture was poured into saturated aqueous $NaHCO_3$ (50 mL) and the organic layer was removed. The aqueous layer was extracted with dichloromethane (3×50 mL) and the combined organic layers were dried over $Na_2SO_4$, filtered, and concentrated by rotary evaporation. The residue was purified by flash chromatography using the CombiFlash (80 g column, 1 to 15% EtOAc in hexanes) to afford S7 (2.6 g, 93% yield) as a white solid.

(8S,9S,10R,13S,14S,17S)-17-((E)-1-(4-(aminomethyl)benzoyloxyimino)ethyl)-10,13-dimethyl-6,7,8,9,10,11,12,13,14,15,16,17-dodecahydro-1H-cyclopenta[a]phenanthren-3(2H)-one (16):

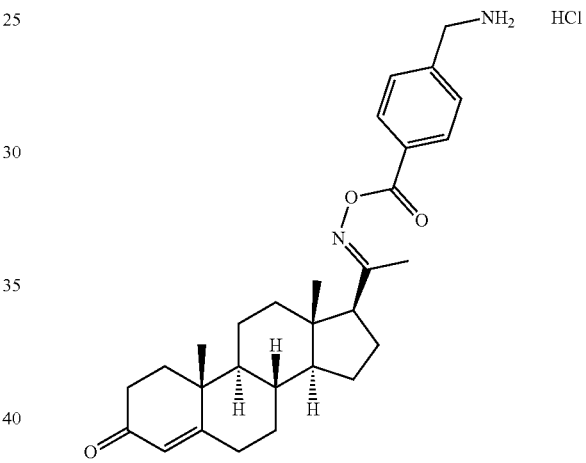

A round bottom flask was charged with S7 (2.25 g, 4.00 mmol) and dichloromethane (12 mL) under nitrogen, and the stirred solution was cooled to 0° C. TFA (12 mL, 160 mmol) was added dropwise by syringe over 10 min, and stirring was continued at 0° C. for 1 h. The volatiles were removed under reduced pressure and the residue was dried in vacuo. The brown oil was dissolved in THF (6 mL), the solution was cooled to 0° C., and treated with a 4.0 M HCl-dioxane solution (1.25 mL, 5.0 mmol) over a 10 minute period. The mixture was stirred an additional 30 minutes at 0° C., and ether (120 mL) was added, during which a white precipitate formed. The mixture was stirred an additional 15 min at 0° C., the supernatant was decanted, and the solid was triturated twice with ether (2×120 mL) at 0° C. The solid was dried in vacuo to afford 16 (1.90 g, 95% yield) as a white solid.

(8S,9S,10R,13S,14S,17S)-10,13-dimethyl-17-((E)-1-(4-((4-methylpiperazin-1-yl)methyl)benzoyloxyimino)ethyl)-6,7,8,9,10,11,12,13,14,15,16,17-dodecahydro-1H-cyclopenta[a]phenanthren-3(2H)-one (17). See Seeliger et al., Cancer Research, 2009, 69(6), 2384-2392.

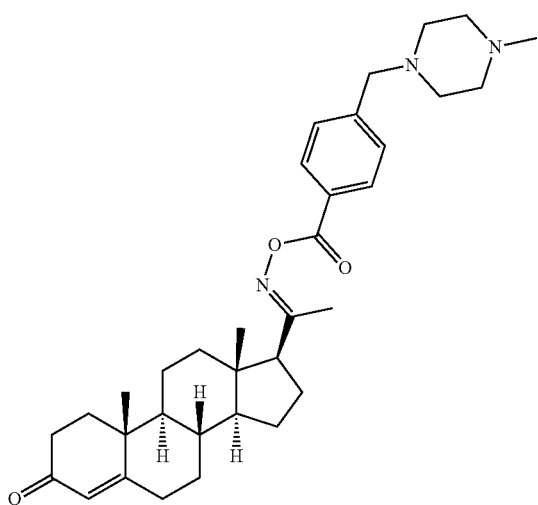

A round bottom flask was charged with 3 (0.66 g, 2.0 mmol), 4-((4-methylpiperazin-1-yl)methyl)benzoic acid (1.27 g, 4.0 mmol), DMAP (0.049 g, 0.40 mmol), and dichloromethane (20 mL) under nitrogen with stirring. The mixture was cooled to 0° C. using an ice bath, and N,N-diisopropylethylamine (2.09 mL, 12.0 mmol) was added, followed by the addition of solid EDCI (0.77 g, 4.0 mmol) in one portion. The mixture was slowly warmed to ambient temperature and stirred for 18 h. The mixture was poured into saturated aqueous NaHCO₃ (20 mL), the organic layer was removed, and the aqueous layer was extracted with dichloromethane (3×40 mL). The combined organic layers were dried over Na₂SO₄, filtered, and concentrated by rotary evaporation. The residue was purified by flash chromatography using the CombiFlash (40 g column, 1 to 10% MeOH in dichloromethane) to afford 17 (0.68 g, 62% yield) as a white solid.

tert-Butyl 4-(((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylideneaminooxy)carbonyl)piperidine-1-carboxylate (S8). See Klein et al., J. Med. Chem. 1998, 41, 2492-2502.

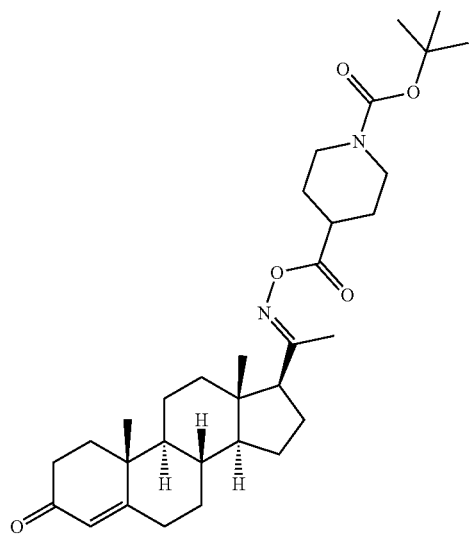

A round bottom flask was charged with 3 (1.65 g, 5.00 mmol), 1-(tert-butoxycarbonyl)piperidine-4-carboxylic acid9 (2.29 g, 10.0 mmol), DMAP (0.061 g, 0.50 mmol) and dichloromethane (50 mL) under nitrogen with stirring. The solution was cooled to 0° C., and N,N-diisopropylethylamine (1.742 ml, 10.00 mmol) was added via syringe. Solid EDCI (1.92 g, 10.0 mmol) was added in one portion and the solution was warmed to ambient temperature. After stirring for 18 h, saturated aqueous NaHCO₃ (50 mL) was added, the organic layer was removed, and the aqueous layer was extracted with dichloromethane (3×50 mL). The combined organic layers were dried over Na₂SO₄, filtered, and concentrated by rotary evaporation. The resulting oil was purified by flash chromatography using a CombiFlash (80 g column, 1 to 40% EtOAc in DCM) to afford S8 (2.57 g, 95% yield) as a white solid.

(8S,9S,10R,13S,14S,17S)-10,13-Dimethyl-17-((E)-1-(piperidine-4-carbonyloxyimino)ethyl)-6,7,8,9,10,11,12,13,14,15,16,17-dodecahydro-1H-cyclopenta[a]phenanthren-3(2H)-one hydrochloride (18).

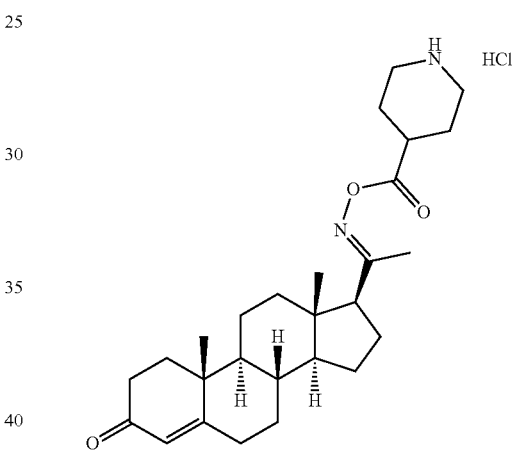

A round bottom flask was charged with S8 (2.16 g, 4.0 mmol) and dichloromethane (12 mL) at 0° C. under nitrogen. TFA (12 mL, 160 mmol) was added dropwise via syringe to the stirred solution over 10 minutes, and the mixture was stirred an additional 1.5 hours at 0° C. The volatiles were removed by rotary evaporation, and the residue was further dried in vacuo. The residue was dissolved in THF (6 mL), cooled to 0° C. under nitrogen with stirring, and treated with a 4.0 M HCl-dioxane solution (1.25 mL, 5.00 mmol). The mixture was stirred for 30 minutes at 0° C., then ether (120 mL) was slowly added and stirring was continued for an additional 15 minutes at 0° C., during which time a white precipitate formed. The supernatant was decanted, and the solid was triturated twice more with ether (2×120 mL) and dried in vacuo to afford 18 (1.84 g, 96% yield) as a white solid.

(8S,9S,10R,13S,14S,17S)-10,13-Dimethyl-17-((E)-1-(1-methylpiperidine-4-carbonyloxyimino)ethyl)-6,7,8,9,10,11,12,13,14,15,16,17-dodecahydro-1H-cyclopenta[a]phenanthren-3(2H)-one (19). See Gray et al., J. Med. Chem., 1988, 31(4), 807-14.

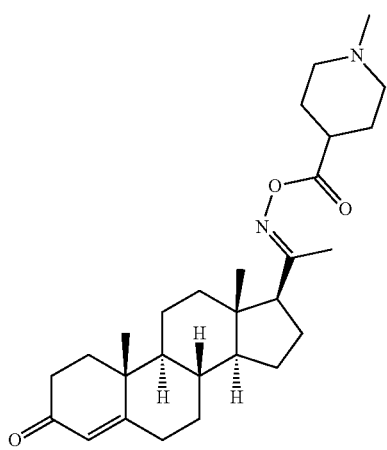

A round bottom flask was charged with 3 (1.65 g, 5.00 mmol), 1-methylpiperidine carboxylic acid hydrochloride (1.78 g, 10.0 mmol), DMAP (0.061 g, 0.50 mmol), and dichloromethane (100 mL) under nitrogen with stirring. The mixture was cooled to 0° C., and DIPEA (1.74 mL, 10.0 mmol) was added via syringe. Solid EDCI (1.92 g, 10.0 mmol) was added in one portion, the mixture was warmed to ambient temperature and stirred 18 h. Saturated aqueous NaHCO$_3$ (100 mL) was added, the organic layer was removed, and the aqueous layer was extracted with dichloromethane (3×100 mL). The combined organic layers were dried over Na$_2$SO$_4$, filtered, and concentrated by rotary evaporation. The residue was purified by flash chromatography using a Combiflash (80 g column, 1 to 10% MeOH in DCM) to afford 19 (1.68 g, 74% yield) as an off-white solid.

(8S,9S,10R,13S,14S,17S)-10,13-Dimethyl-17-((E)-1-(1,1-dimethylpiperidine-4-carbonyloxyimino)ethyl)-6,7,8,9,10,11,12,13,14,15,16,17-dodecahydro-1H-cyclopenta[a]phenanthren-3(2H)-one iodide (20).

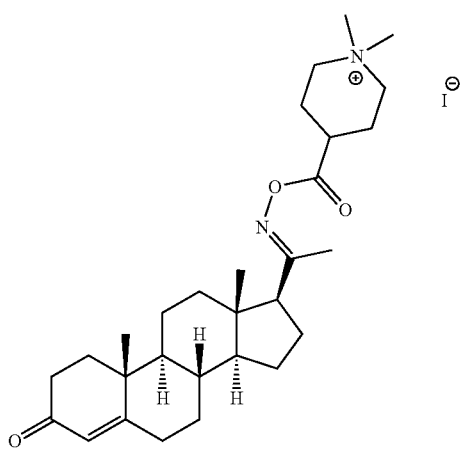

A round bottom flask was charged with 19 (0.23 g, 0.50 mmol) and acetone (10 mL) at room temperature under nitrogen. To the stirred solution was added iodomethane (0.31 ml, 5.00 mmol) all at once via syringe, and the mixture was heated to reflux with stirring for 1 h. A white precipitate formed during this time. The mixture was cooled to room temperature, the supernatant was removed, and the solid was triturated with acetone (2×10 mL). The solid was dried in vacuo to afford 20 (0.24 g, 80% yield) as a white solid.

(R)-tert-Butyl 3-(((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylideneaminooxy)carbonyl)piperidine-1-carboxylate (S9). Hauske, WO 201020889 and Hayashi et al., J. Med. Chem., 2009, 52 (3), 610-625.

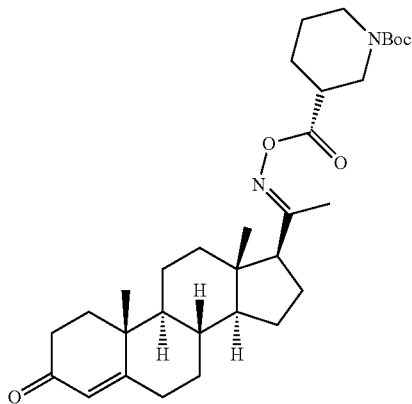

A round bottom flask was charged with 3 (0.99 g, 3.0 mmol), 1-(tert-butoxycarbonyl)piperidine-3R-carboxylic acid (1.38 g, 6.00 mmol), DMAP (0.037 g, 0.30 mmol) and dichloromethane (20 mL) under nitrogen with stirring. The mixture was cooled to 0° C., and N,N-diisopropylethylamine (1.05 mL, 6.00 mmol) was added via syringe, followed by solid EDCI (1.15 g, 6.00 mmol). The mixture was slowly warmed to ambient temperature and stirred for 18 h. Saturated aqueous NH$_4$Cl (20 mL) was added, and the organic layer was removed. The aqueous layer was extracted with dichloromethane (3×30 mL), and the combined organic layers were washed with brine (1×40 mL), dried over Na$_2$SO$_4$, filtered, and concentrated by rotary evaporation. The crude material was purified using a Combiflash (80 g column, 1 to 20% EtOAc in DCM) to afford S9 (1.53 g, 94% yield) as a white, fluffy solid.

(8S,9S,10R,13S,14S,17S)-10,13-dimethyl-17-((E)-1-((R)-piperidine-3-carbonyloxyimino)ethyl)-6,7,8,9,10,11,12,13,14,15,16,17-dodecahydro-1H-cyclopenta[a]phenanthren-3(2H)-one hydrochloride (21).

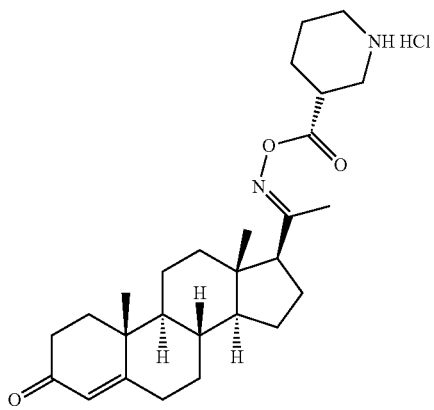

A round bottom flask was charged with S9 (1.40 g, 2.59 mmol) and dichloromethane (8.0 mL) under nitrogen, and the stirred solution was cooled to 0° C. The solution was treated with TFA (8.1 mL) dropwise via syringe. The mixture was stirred for 1 h at 0° C., and volatiles were removed by rotary evaporation followed by high vacuum. The residue was treated with a 4.0 M HCl-dioxane solution (0.81 mL, 3.24 mmol) dropwise via syringe under nitrogen at 0° C., and the mixture was stirred for 15 minutes. Ether (100 mL) was added and the mixture was stirred an additional 20 minutes. The supernatant was removed, and the precipitate was triturated twice with ether (2×100 mL). The solid was dried in vacuo to yield 1.11 g of 21(1.11 g, 90% yield) as a white powder.

(S)-tert-Butyl 3-(((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylideneaminooxy)carbonyl)piperidine-1-carboxylate (S10).

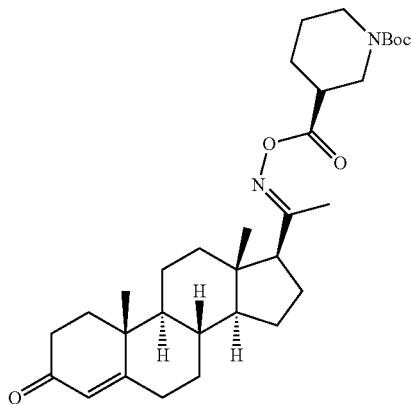

Prepared as above for S9 starting with 1-(tert-butoxycarbonyl)piperidine-3S-carboxylic acid to afford 1.52 g of S10 (1.52 g, 94%) as a white, fluffy solid in 94% yield.

(8S,9S,10R,13S,14S,17S)-10,13-Dimethyl-17-((E)-1-((S)-piperidine-3-carbonyloxyimino)ethyl)-6,7,8,9,10,11,12,13,14,15,16,17-dodecahydro-1H-cyclopenta[a]phenanthren-3(2H)-one hydrochloride (22).

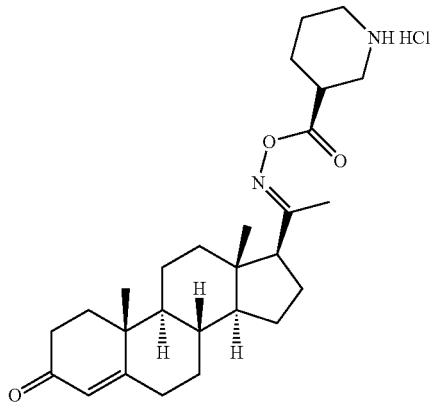

Prepared as above for 21 to afford 22 (1.07 g, 92% yield) as a white solid.

(E)-1-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)ethanone O-ethyl oxime (S11).

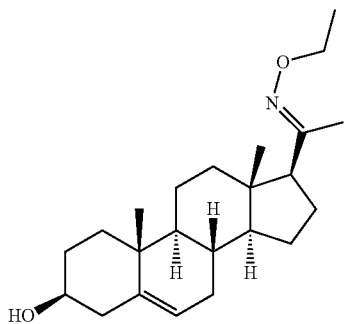

A round bottom flask was charged with 5-pregnen-3β-ol-20-one (3.16 g, 10.0 mmol), O-ethylhydroxylamine hydochloride (1.07 g, 11.0 mmol), and pyridine (10 mL) under nitrogen. The stirred mixture was heated at 95° C. for 18 h, cooled to room temperature, poured into water (100 mL), and stirred for 15 min. The white solid was collected by filtration, washed with water, and dried in vacuo. The solid was purified by flash chromatography (9:1 DCM:EtOAc) to afford S11 (3.49 g, 97% yield) as a white solid.

(8S,9S,10R,13S,14S,17S)-17-((E)-1-(Ethoxyimino)ethyl)-10,13-dimethyl-6,7,8,9,10,11,12,13,14,15,16,17-dodecahydro-1H-cyclopenta[a]phenanthren-3(2H)-one (S12).

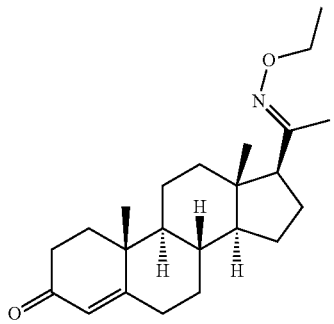

A round bottom flask fitted with a reflux condenser and Dean-Stark trap was charged with S11 (1.44 g, 4.00 mmol), N-methyl-4-piperidone (4.53 g, 40 mmol) and toluene (40 mL) with stirring. The mixture was heated to reflux for 1 hr with azeotropic removal of adventitious water, recooled to ambient temperature, and aluminum isopropoxide (1.63 g, 8.00 mmol) was added all at once. After refluxing for 18 h, the mixture was cooled to ambient temperature and treated with a saturated solution of Rochelle's salt (20 mL) for 1 h. The organic layer was removed, and the aqueous layer was extracted with DCM (3×20 mL). The combined organic layers were washed with water (3×20 mL) and brine (3×20 mL), dried over $Na_2SO_4$, filtered, and concentrated by rotary evaporation. The dark orange solid was purified by flash chromatography (4:1 hexanes:EtOAc) to afford S12 (0.83 g, 55% yield) as a white solid (8S,9S,10R,13S,14S,17S)-17-((E)-1-(2-bromoethoxyimino)ethyl)-10,13-dimethyl-6,7,8,9,10,11,12,13,14,15,16,17-dodecahydro-1H-cyclopenta[a]phenanthren-3(2H)-one (S13).

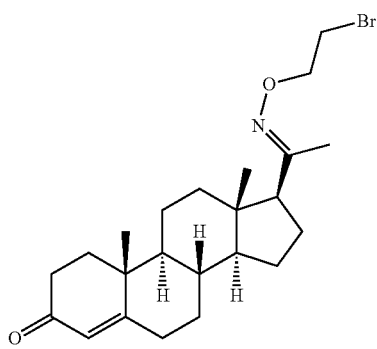

A round bottom flask was charged with 3 (1.97 g, 6.0 mmol) and dichloromethane (12 mL) with stirring. 1,2-dibromoethane (22.5 g, 120 mmol) was added via syringe all at once, followed by solid tetrabutylammonium bromide (5.80 g, 18.0 mmol) in one portion, and 10% aqueous NaOH solution (24 mL) all at once. The mixture was stirred at ambient temperature for 48 h, the organic layer was removed, and the aqueous layer was extracted with dichloromethane (3×50 mL). The combined organic layers were washed with brine (2×50 mL), dried over sodium sulfate, filtered, and concentrated by rotary evaporation. The residue was purified by silica gel chromatography (20:1 $CH_2Cl_2$/EtOAc) to afford S13 (1.32 g, 51% yield) as an off-white solid.

(8S,9S,10R,13S,14S,17S)-10,13-dimethyl-17-((E)-1-(2-propylpentanoyloxyimino)ethyl)-6,7,8,9,10,11,12,13,14,15,16,17-dodecahydro-1H-cyclopenta[a]phenanthren-3(2H)-one (S15).

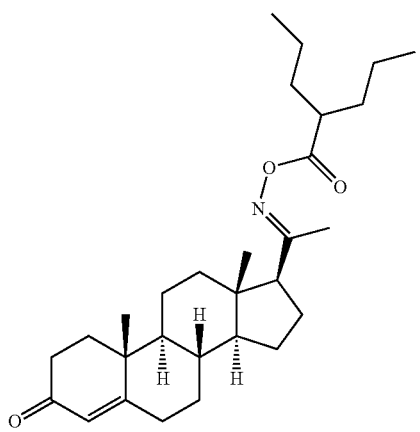

A round bottom flask was charged with 3 (0.66 g, 2.00 mmol), valproic acid sodium salt (1.00 g, 6.00 mmol) and dichloromethane (20 mL) under nitrogen with stirring. To the solution was added DMAP (0.073 g, 0.60 mmol) and N,N-diisopropylethylamine (1.05 mL, 6.00 mmol), followed by solid EDCI (1.15 g, 6.00 mmol) in one portion. After stirring for 16 h at ambient temperature, the reaction was quenched by the addition of water (20 mL) and the organic layer was removed. The aqueous layer was extracted with dichloromethane (3×20 mL). The combined organic layers were washed with water (3×20 mL) and brine (1×20 mL), dried over $Na_2SO_4$, filtered, and concentrated by rotary evaporation. The residue was purified using the Combiflash (0 to 30% EtOAc in DCM) to afford S15 (0.73 g, 79% yield) as a white solid.

(8S,9S,10R,13S,14S,17S)-10,13-Dimethyl-17-((E)-1-(4-(morpholinomethyl)benzoyloxyimino)ethyl)-6,7,8,9,10,11,12,13,14,15,16,17-dodecahydro-1H-cyclopenta[a]phenanthren-3(2H)-one (S16). See Moradei et al., WO 2005030704.

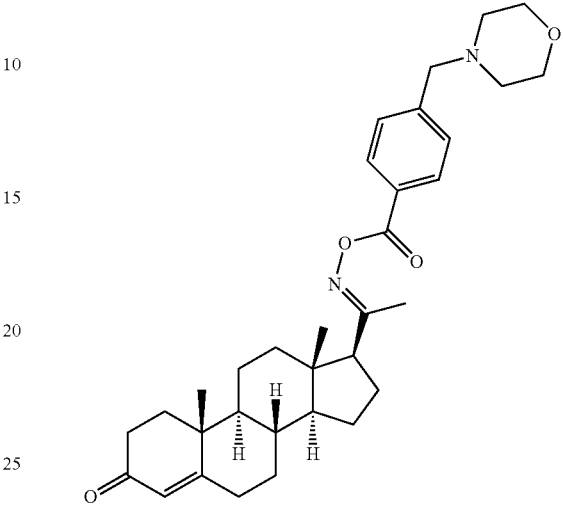

A round bottom flask was charged with 3 (0.66 g, 2.0 mmol), 4-(morpholinomethyl)benzoic acid (0.89 g, 4.0 mmol), DMAP (0.049 g, 0.40 mmol) and dichloromethane (50 mL) under nitrogen with stirring. The resulting solution was cooled to 0° C., N,N-diisopropylethylamine (0.70 mL, 4.0 mmol) was added, followed by solid EDCI (0.77 g, 4.0 mmol) in one portion. The mixture was warmed to ambient temperature and stirred for 18 h. Saturated aqueous $NaHCO_3$ (20 mL) was added, the organic layer was removed, and the aqueous layer was extracted with dichloromethane (3×50 mL). The combined organic layers were dried over $Na_2SO_4$, filtered, and concentrated by rotary evaporation. The residue was purified using the Combiflash (40 g column, 1 to 50% EtOAc in DCM) to afford S16 (1.01 g, 95% yield) as a white solid.

General procedure for hydrolytic stability testing:

A small amount of the parent compound (0.1-0.3 mg/mL) was dissolved in 10 mM pH 6.97 phosphate buffer, and the mixture was sonicated for 5 min. The solution was filtered through a 0.2 μM PES HPLC filter to remove insoluble material. A sample was immediately analyzed by LCMS; this was taken as t=0. The same filtered sample was kept at 23° C. and reinjected at regular intervals without additional filtration or other sample preparation. Insoluble oxime gradually precipitated, but this did not affect the results. The area of the parent peak for each LC was measured by automated integration. In each case, the baseline was flat with excellent peak separation, peaks were well-defined, and only two peaks were seen (parent compound and oxime degradation product).

Pseudo first-order half-lives were calculated by determining the percent of parent compound remaining at each timepoint. Time (x-axis) was plotted against the natural logarithm of the percent parent remaining (y-axis), the slope/intercept of the line was determined, and the following equation was used:

$$t^{1/2} = [\ln(50) - yint]/\text{slope}$$

LC Conditions

Injection volume: 10 μL

Column temperature: 40° C.

Detector: 254 nm

Stationary Phase: Zorbax Eclipse XDB-C18 4.6×150 mm ID

Flow Rate: 1 mL/min

Mobile Phase: isocratic MeCN, pH 3 $HCO_2H/HCO_2NH_4$ buffer (see table for proportions used for each compound)

In Vitro Experiments

Primary cortical cells were seeded in multi-well plates and cultured for 8 days before treatment. Cells were pre-treated with various concentrations of different PROG analogues (0.1, 1, 5, 10, 20, 40, 80 μM) for 24 h. Then cells were then exposed to glutamate (0.5 μM) for the next 24 h. The following two widely accepted cell death assays were adopted for the evaluation of neuroprotective effect of various PROG analogues.

MTT assay. Cytotoxicity was assessed by the MTT [3-(4,5-dimethylthiazol-2-yl)-2,5-diphenyltetrazolium bromide] assay, which is based on the ability of a mitochondrial dehydrogenase enzyme from viable cells to cleave the tetrazolium rings of the pale yellow MTT. This reaction forms dark blue formazan crystals which are largely impermeable to cell membranes, thus resulting in their accumulation within healthy cells. Solubilization of the cells results in the liberation of the crystals, which are then also solubilized. The number of surviving cells is directly proportional to the level of the formazan product created. Concentrations were determined by photometric analysis.

LDH Release Assay. Cytotoxicity is assessed by measuring the intracellular lactate dehydrogenase (LDH) leakage in the medium by means of a kinetic photometric assay. This is widely recognized as a cytotoxic end-point indicator for cell membrane disruption and viability. The higher the LDH activity, the higher the cell death.

Example 3

Cerebral Edema Assay Methods

Surgery—Contusions to the medio-frontal cortex (MFC) were created with a pneumatic impactor device. Animals were anesthetized using isoflurane (5% induction, 2% maintenance, 700 mm $N_2O$, 300 mm $O_2$), and mounted in a stereotaxic device with the head in a horizontal position. The body core temperature was maintained with a homeothermic heating blanket system. Using a SurgiVet™ (model V3304) pulse oximeter, blood $SpO_2$ was monitored and maintained at levels ≥90%. Under aseptic conditions, a midline incision was made in the scalp and the fascia retracted to expose the cranium. A centered, bilateral craniotomy was made 3 mm anterior to bregma using a 6 mm diameter trephan. After the removal of the bone, the tip of the impactor was moved to AP: 3.0; ML: 0.0, checked for adequate clearance, retracted to its elevated position, and lowered 3.5 mm DV. The contusion was then made at a velocity of 2.25 m/s with a brain contact time of 0.5 seconds. Following this procedure, the wound cavity was thoroughly cleaned and all bleeding stopped before the fascia and scalp were sutured closed.

Progestin preparation and administration—Experimental treatments by injection (progesterone and analogues) were made in stock solutions using 2-hydroxypropyl-β-cyclodextrin (HBC; 22.5% w/v solution in $H_2O$) as the solvent. The HBC vehicle allows progesterone and analogues to be dissolved in a non-toxic, aqueous solution which can be administered safely by a variety of routes. The initial dose of progesterone or analogue given at 1 h post-injury was delivered intraperitoneally (IP) for rapid absorption followed by a subcutaneous injection at 6 h post-injury.

Edema measure—At 24 h post-injury, animals were given an IP overdose of pentobarbital (75 mg/kg). The pericontusional tissue samples from each area were assayed for water content as follows: samples were placed into pre-weighed containers, capped, and then immediately weighed to the nearest 0.0001 g. The containers were then uncapped and placed in a vacuum oven and dried at 60° C., 0.3 atm for 24 h. The containers were then recapped and reweighed to obtain the dry and wet-weight percentages. A "% mean difference" value could then be calculated based on the relative edema difference between injured and non-injured tissue samples for a given animal.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A compound of the following formula:

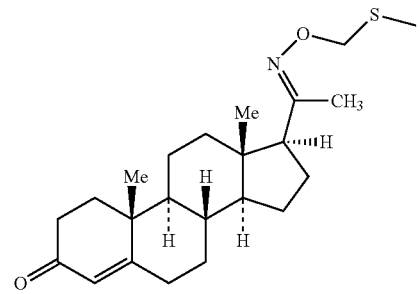

or a pharmaceutically acceptable salt thereof.

2. A pharmaceutical composition comprising the compound of claim 1, or a pharmaceutically acceptable salt thereof, and a pharmaceutically acceptable excipient.

3. The pharmaceutical composition of claim 2, further comprising a second active therapeutic agent.

4. The pharmaceutical composition of claim 3, wherein the second active therapeutic agent is an anti-inflammatory agent.

5. A method of reducing the symptoms of or delaying the progression of stroke or traumatic brain injury, comprising administering at least one effective amount of the compound of claim 1, or a pharmaceutically acceptable salt thereof.

6. The method of claim 5, wherein the compound, or a pharmaceutically acceptable salt thereof, is administered to a subject that incurred trauma to the head or other organ or tissue.

7. The method of claim 5, wherein the compound, or a pharmaceutically acceptable salt thereof, is administered to the subject after a medical procedure.

8. The method of claim 5, wherein the compound, or a pharmaceutically acceptable salt thereof, is administered in combination with a second active therapeutic agent.

9. The method of claim 8, wherein the second active therapeutic agent is an anti-inflammatory agent.

10. The method of claim 5, wherein the stroke is an ischemic stroke.

11. The method of claim 5, wherein the stroke is a hemorrhagic stroke.

12. The method of claim 5, wherein the traumatic brain injury comprises at least one of a skull fracture, parenchymal injury, and vascular injury.

13. The method of claim 12, wherein vascular injury comprises a hemorrhage.

14. A method of reducing the symptoms of or delaying the progression of stroke or traumatic brain injury, comprising administering at least one effective amount of the pharmaceutical composition of claim 2.

15. The method of claim 14, wherein the pharmaceutical composition is administered to a subject that incurred trauma to the head or other organ or tissue.

16. The method of claim 14, wherein the pharmaceutical composition is administered to the subject after a medical procedure.

17. The method of claim 14, wherein the pharmaceutical composition is administered in combination with a second active therapeutic agent.

18. The method of claim 17, wherein the second active therapeutic agent is an anti-inflammatory agent.

19. The method of claim 14, wherein the stroke is an ischemic stroke or hemorrhagic stroke.

20. The method of claim 14, wherein the traumatic brain injury comprises at least one of a skull fracture, parenchymal injury, and vascular injury.

* * * * *